United States Patent
Su

(10) Patent No.: US 10,420,798 B2
(45) Date of Patent: Sep. 24, 2019

(54) METHOD FOR TREATING LUNG INJURY AND/OR DISEASES RELATED TO LUNG INJURY

(71) Applicant: TAIWAN MITOCHONDRION APPLIED TECHNOLOGY CO., LTD, Hsinchu County (TW)

(72) Inventor: Hong-Lin Su, Taichung (TW)

(73) Assignee: TAIWAN MITOCHONDRION APPLIED TECHNOLOGY CO., LTD, Zhubei, Hsinchu County (TW)

( * ) Notice: Subject to any disclaimer, the term of this patent is extended or adjusted under 35 U.S.C. 154(b) by 0 days.

(21) Appl. No.: 15/541,192

(22) PCT Filed: Dec. 31, 2014

(86) PCT No.: PCT/CN2014/095846
§ 371 (c)(1),
(2) Date: Jun. 30, 2017

(87) PCT Pub. No.: WO2016/106660
PCT Pub. Date: Jul. 7, 2016

(65) Prior Publication Data
US 2017/0340668 A1    Nov. 30, 2017

(51) Int. Cl.
*A61K 31/4045* (2006.01)
*A61K 35/12* (2015.01)
*A61K 35/407* (2015.01)

(52) U.S. Cl.
CPC .......... *A61K 35/12* (2013.01); *A61K 31/4045* (2013.01); *A61K 35/407* (2013.01)

(58) Field of Classification Search
None
See application file for complete search history.

(56) References Cited

U.S. PATENT DOCUMENTS

| | | | | |
|---|---|---|---|---|
| 2015/0079193 A1* | 3/2015 | Yivgi-Ohana | ......... | A61K 35/14 424/529 |
| 2018/0028498 A1* | 2/2018 | Perillo | ................. | A61K 9/0019 |

FOREIGN PATENT DOCUMENTS

| WO | 2005102319 A1 | 11/2005 |
|---|---|---|
| WO | 2013171752 A1 | 11/2013 |

OTHER PUBLICATIONS

Yip H. K. et al. Systemic Administration of Mitochondria Alleviates 100% Oxygen Induced Acute Respiratory Distress Syndrome in Rats. European Heart J 35(Suppl 1)615, Sep. 1, 2014. (Year: 2014).*
Sun C. et al. Systemic Combined Melatonin Mitochondria Treatment Improves Acute Respiratory Distress Syndrome in the Rat. J of Pineal Research 58(2)137-150, Mar. 2015. (Year: 2015).*
Brun-Buisson et al., Epidemiology and outcome of acute lung injury in European intensive care units, Intensive Care Med., 2004, pp. 51-61, 30.
Matthay et al., Acute Lung Injury and the Acute Respiratory Distress Syndrome, American Journal of Respiratory Cell and Molecular Biology, 2005, pp. 319-327, vol. 33.
Rubenfeld et al., Incidence and Outcomes of Acute Lung Injury, The New England Journal of Medicine, 2005, pp. 1685-1693, 353;16.
Phua et al., Has Mortality from Acute Respiratory Distress Syndrome Decreased over Time? American Journal of Respiratory and Critical Care Medicine, 2009, pp. 220-227, vol. 179.
Ailawadi et al., Does reperfusion injury still cause significant mortality after Lung Transplantation? The Journal of Thoracic and Cardiovascular Surgery, 2009, pp. 688-694.
Fiser et al., Ischemia-Reperfusion Injury After Lung Transplantation Increases Risk of Late Bronchiolitis Obliterans Syndrome, Ann. Thorac. Surg., 2002, pp. 1041-1048, 73.
Ware et al., The Acute Respiratory Distress Syndrome, The New England Journal of Medicine, 2000, pp. 1334-1349, vol. 342, No. 18.
Ciesla et al., The Role of the Lung in Postinjury Multiple Organ Failure, Surgery, 2005, pp. 749-758.
Den Hengst et al., Lung ischemia-reperfusion injury: a molecular and clinical view on a complex pathophysiological process, Am. J. Physiol. Heart Circ. Physiol., 2010, pp. H1283-H1299, 299.
Choi et al., Markers of Poor Outcome in patients with acute hypoxemic respiratory failure, Journal of Critical Care, 2014.
Dolinay et al., Inflammasome-Regulated Cytokines Are Critical Mediators of Acute Lung Injury, American Journal of Respiratory and Critical Care Medicine, 2012, pp. 1225-1234, vol. 185.
Bhargava et al., Biomarkers in Acute Lung Injury, Transl. Res., 2012, pp. 205-217, 159(4).
Sun et al., Autologous Transplantation of Adipose-Derived Mesenchymal Stem Cells Markedly Reduced Acute Ischemia-Reperfusion Lung Injury in a Rodent Model, Journal of Translational Medicine, 2011, 9:118.
Budinger et al., Epithelial Cell Death Is an Important Contributor to Oxidant-mediated Acute Lung Injury, American Journal of Respiratory and Critical Care Medicine, 2011, pp. 1043-1054, vol. 183.
Yip et al., Melatonin Treatment Improves Adipose-derived Mesenchymal Stem Cell Therapy for Acute Lung Ischemia-Reperfusion Injury, J. Pineal Res., 2013, pp. 207-221, 54.
State Intellectual Property Office of the P.R. China (ISR/CN), "International Search Report for PCT/CN2014/095846", China, dated Oct. 13, 2015.

* cited by examiner

*Primary Examiner* — Ralph J Gitomer
(74) *Attorney, Agent, or Firm* — Locke Lord LLP; Tim Tingkang Xia, Esq.

(57) ABSTRACT

Disclosed are a novel pharmaceutical composition and use thereof, the novel pharmaceutical composition at least comprising an effective amount of mitochondria and at least one pharmaceutically acceptable carrier; the novel pharmaceutical composition is administered to an individual to send the mitochondria into injured or subject-to-oxidative-stress lung cells; thus treating or improving lung injury or related diseases thereof.

3 Claims, 41 Drawing Sheets

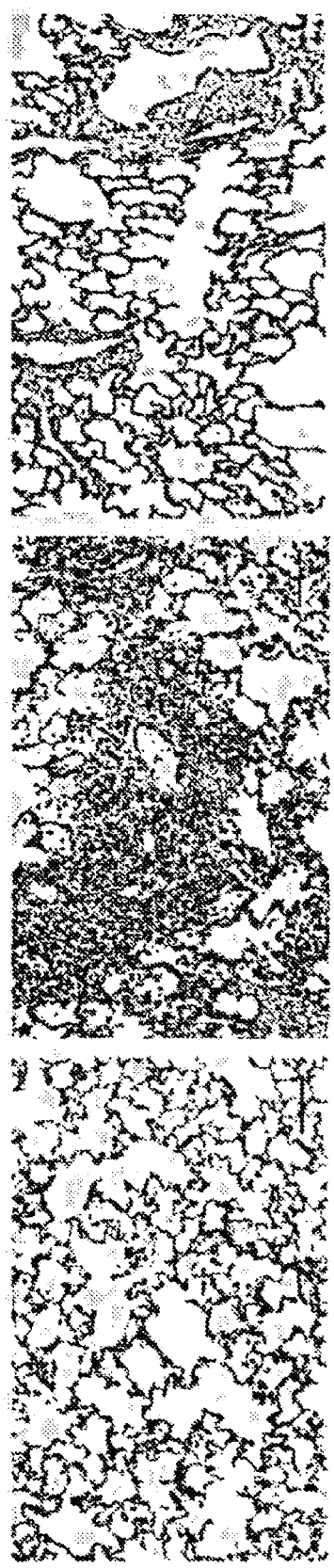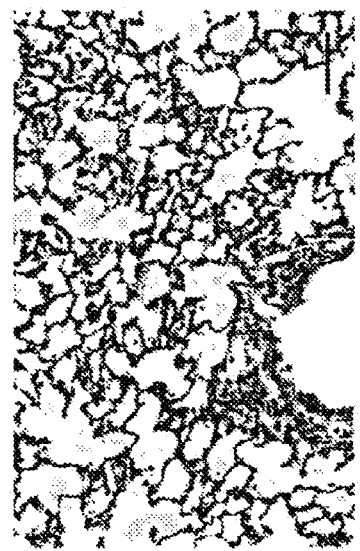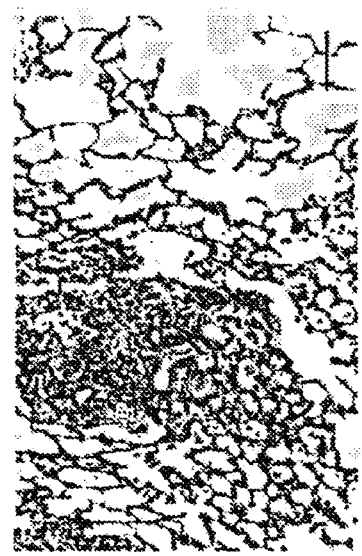

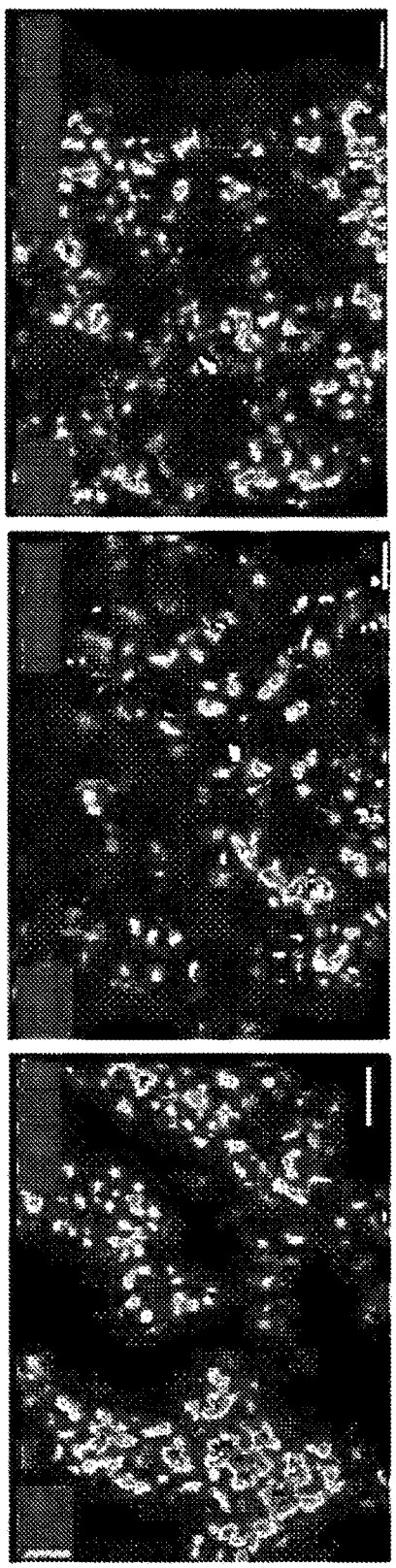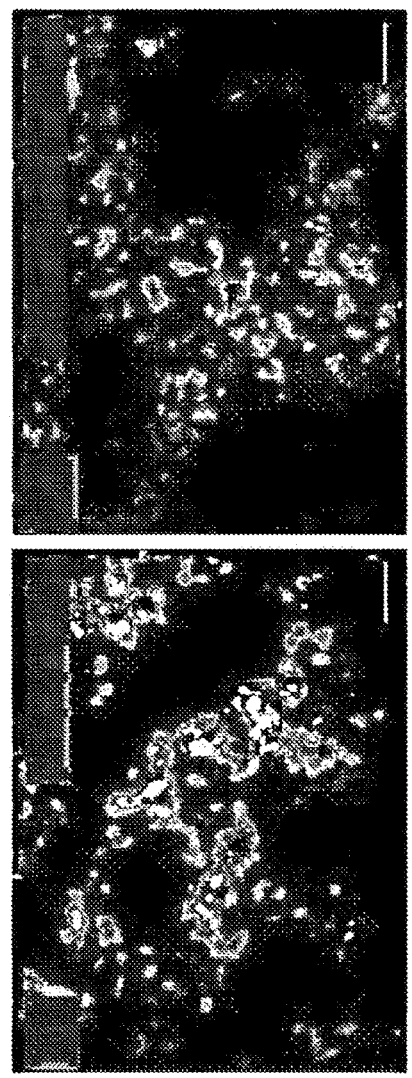

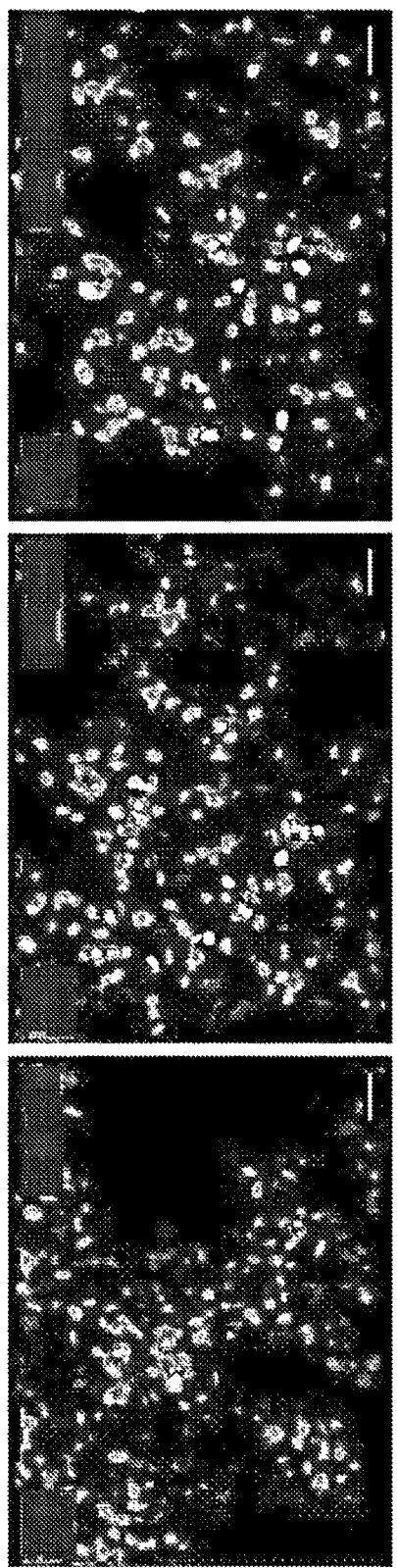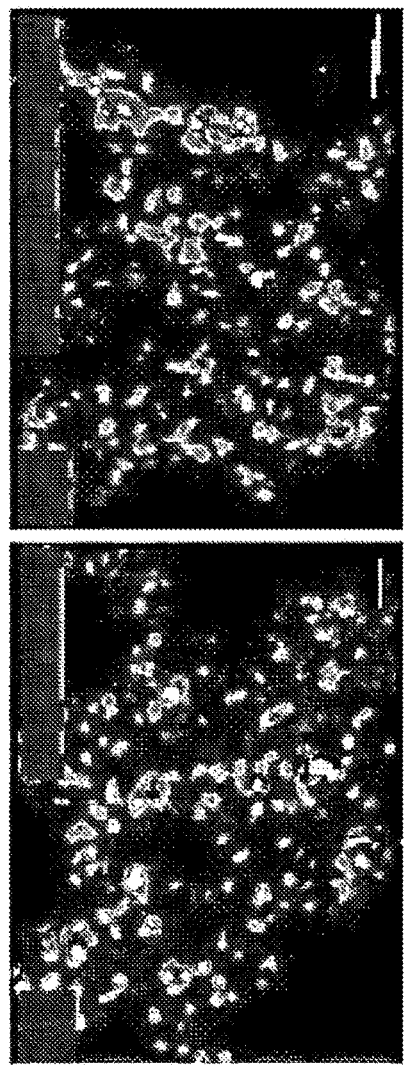

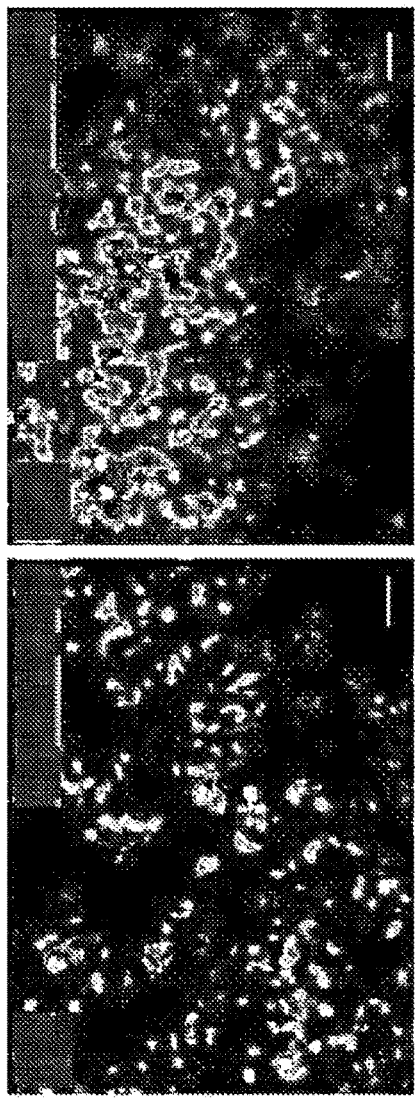
Figure 22A  Figure 22B  Figure 22C  Figure 22D  Figure 22E

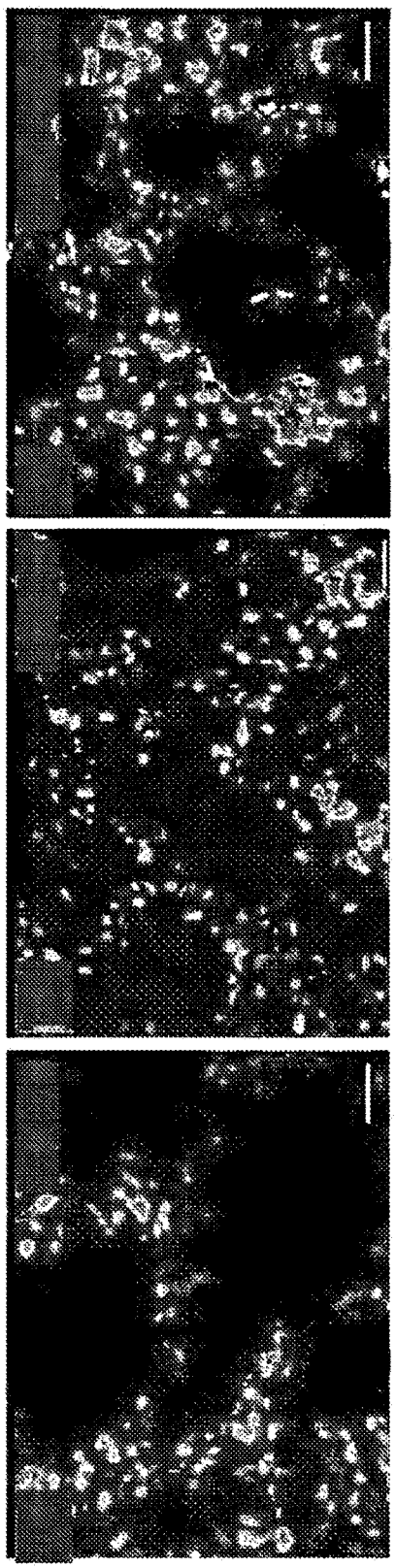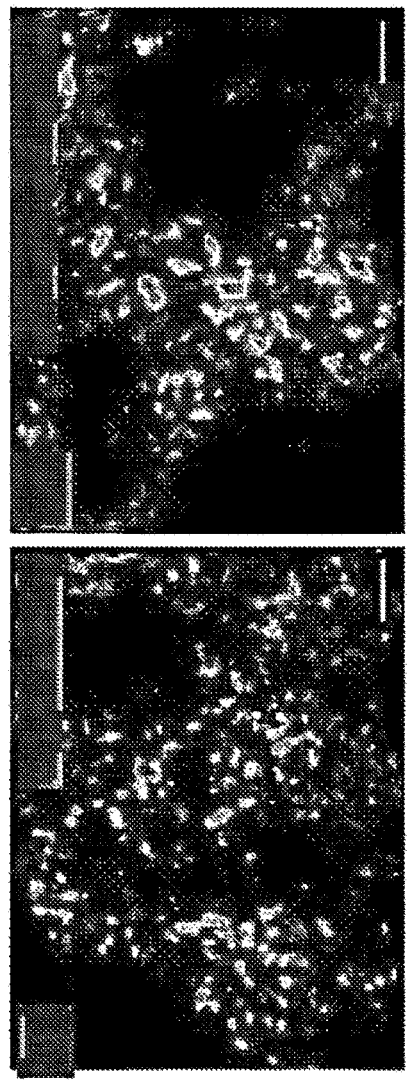
Figure 23A Figure 23B Figure 23C Figure 23D Figure 23E

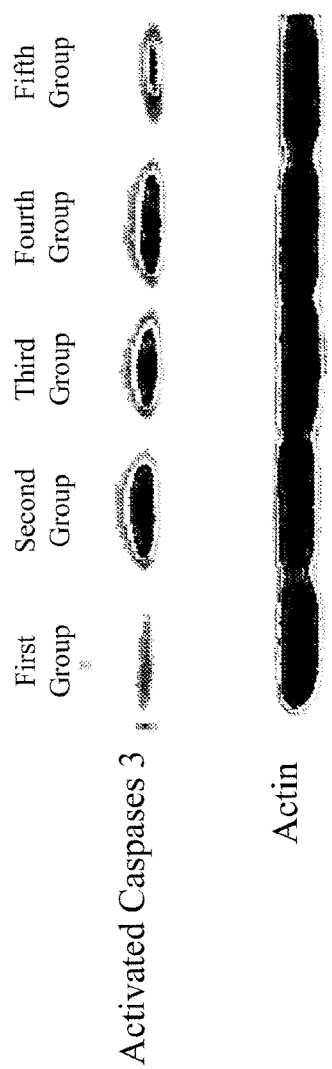
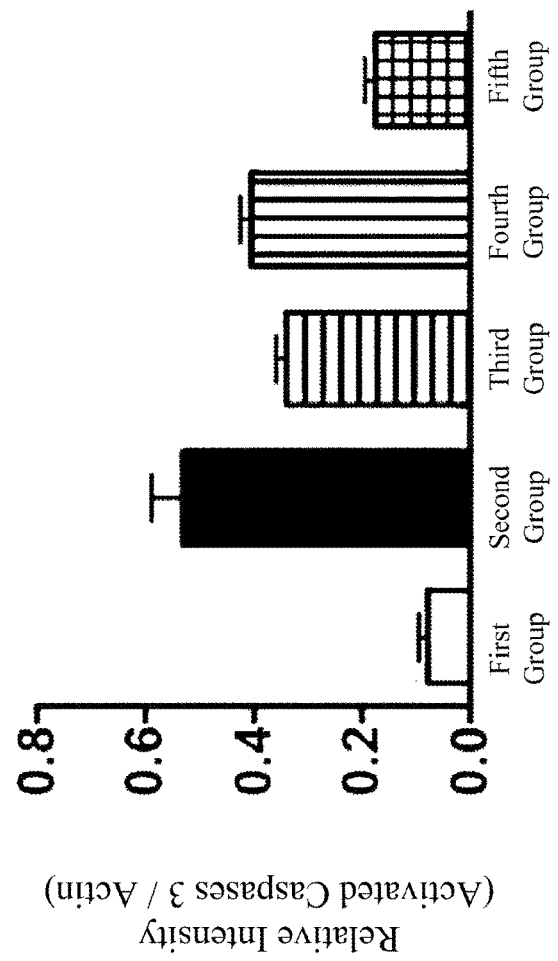
Figure 35A
Figure 35B

METHOD FOR TREATING LUNG INJURY AND/OR DISEASES RELATED TO LUNG INJURY

BACKGROUND OF THE INVENTION

Field of the Invention

The present invention relates to a pharmaceutical composition and use thereof, particularly to a pharmaceutical composition containing mitochondria, which can be used to improve or treat lung injury.

Description of the Prior Art

The lungs are an important organ in the respiratory system, and the organ has soft and elastic sponge-like structure containing 6 to 800 million alveoli. Gaseous exchange in humans is carried out in alveoli and the microvasculatures covered on the surfaces of alveoli. The lungs are a very fragile organ, in which acute lung injury may occur under some circumstances, such as lung transplantation, cardiopulmonary bypass, cardiopulmonary resuscitation, hypoxic respiratory failure, inhalation of smoke, and sepsis, which may lead to acute respiratory distress syndrome (Brun-Buisson C et al., 2004; Matthay M A et al., 2005; Rubenfeld G D et al., 2005; Phua J et al., 2009; Ailawadi G et al., 2009; Fiser S M et al., 2002; Ware L B et al., 2000; Ciesla D J et al., 2005; den Hengst W A et al., 2010).

The so-called acute respiratory distress syndrome is a life-threateningly severe lung injury (Ware L B et al., 2000; Choi W I et al., 2014). According to some studies, acute respiratory distress syndrome and severe lung injury are caused by multiple factors, such as severe inflammatory response, hyperplasia of alveolar leukocytes, protein exuding, oxidation of mitochondria, production of active oxide, increased pulmonary oxidative stress, and apoptosis (Ware L B et al., 2000; den Hengst W A et al., 2010; Dolinay T et al., 2012; Bhargava M et al., 2012; Sun C K et al., 2011; Budinger G R et al., 2011; Yip H K et al., 2013). Although medical care, treatment strategies, and medical instruments for patients with severe diseases keep being improved, and the pathogenesis of acute respiratory distress syndrome is known, supportive therapies, such as use of artificial ventilator and steroids, are still the major treatments for acute respiratory distress syndrome. However, such supportive therapies are ineffective. Therefore, the incidence rate of acute respiratory distress syndrome remains high, which leads to high mortality (Brun-Buisson C et al., 2004; Matthay M A et al., 2005; Rubenfeld G D et al., 2005; Phua J et al., 2009; Ailawadi G et al., 2009). Statistics show that the mortality rate of acute respiratory distress syndrome reaches 40 to 70%.

Accordingly, there is still a lack of a novel and safe treatment regimen that can be used as a clinical treatment of acute respiratory distress syndrome and/or related diseases thereof.

SUMMARY OF THE INVENTION

The primary objective of the present invention is providing a novel pharmaceutical composition comprising an effective amount of mitochondria and at least one pharmaceutically acceptable carrier, and by administering the novel pharmaceutical composition to an individual, the mitochondria can be delivered into specific cells of the individual.

Another objective of the present invention is providing a novel pharmaceutical composition for the treatment or amelioration of lung injury and/or diseases related to lung injury.

In order to achieve the objectives above, an embodiment of the present invention discloses a pharmaceutical composition comprising at least an effective amount of mitochondria and at least one pharmaceutically acceptable carrier. By administering the pharmaceutical composition of the present invention to an individual, the mitochondria can be delivered into the cells to repair cell damage.

Preferably, the pharmaceutical composition further comprises an effective amount of melatonin.

In a particular embodiment of the present invention, the pharmaceutical composition can be used to treat or ameliorate lung injury or diseases related to lung injury. In particular, by administering the pharmaceutical composition to an individual, the mitochondria can enter the lungs to treat or ameliorate lung injury or diseases related to lung injury.

Preferably, the diseases related to lung injury are pneumonia, atelectasis, dyspnea, pulmonary fibrosis, pulmonary edema, and the like.

Preferably, the lung injury is acute respiratory distress syndrome.

The beneficial effects of the present invention are:

By delivering mitochondria into lung cells that are damaged or have oxidative stress, the pharmaceutical composition of the present invention can regain lung capacity, ameliorate pulmonary parenchymal injury induced by acute respiratory distress syndrome, ameliorate oxidative stress, reduce apoptosis of alveolar epithelial cells, and reduce production of oxides, and therefore, improve or treat severe pulmonary parenchymal injury.

BRIEF DESCRIPTION OF THE DRAWINGS

FIGS. 17A to 17E show the images of lung tissue sections of rats in each group stained with hematoxylin and eosin, at 100× magnification.

FIGS. 20A to 20E show the expression of F4/80 in lung tissue sections of rats in each group by immunofluorescence staining, in which the scale bars are 20 μm.

FIGS. 21A to 21E show the expression of γ-H2AX in lung tissue sections of rats in each group by immunofluorescence staining, in which the scale bars are 20 μm.

FIGS. 22A to 22E show the expression of Cx43 in lung tissue sections of rats in each group by immunofluorescence staining, in which the scale bars are 20 μm.

FIGS. 23A to 23E show the expression of heme oxygenase-1 (HO-1) in lung tissue sections of rats in each group by immunofluorescence staining, in which the scale bars are 20 μm.

FIG. 35A shows the expression of activated caspase-3 in lung cells of rats in each group detected by western blotting.

FIG. 35B shows the quantification results of the expression of activated caspase-3 of rats in each group in FIG. 35A.

DETAILED DESCRIPTION OF THE PREFERRED EMBODIMENT

Figure 1:
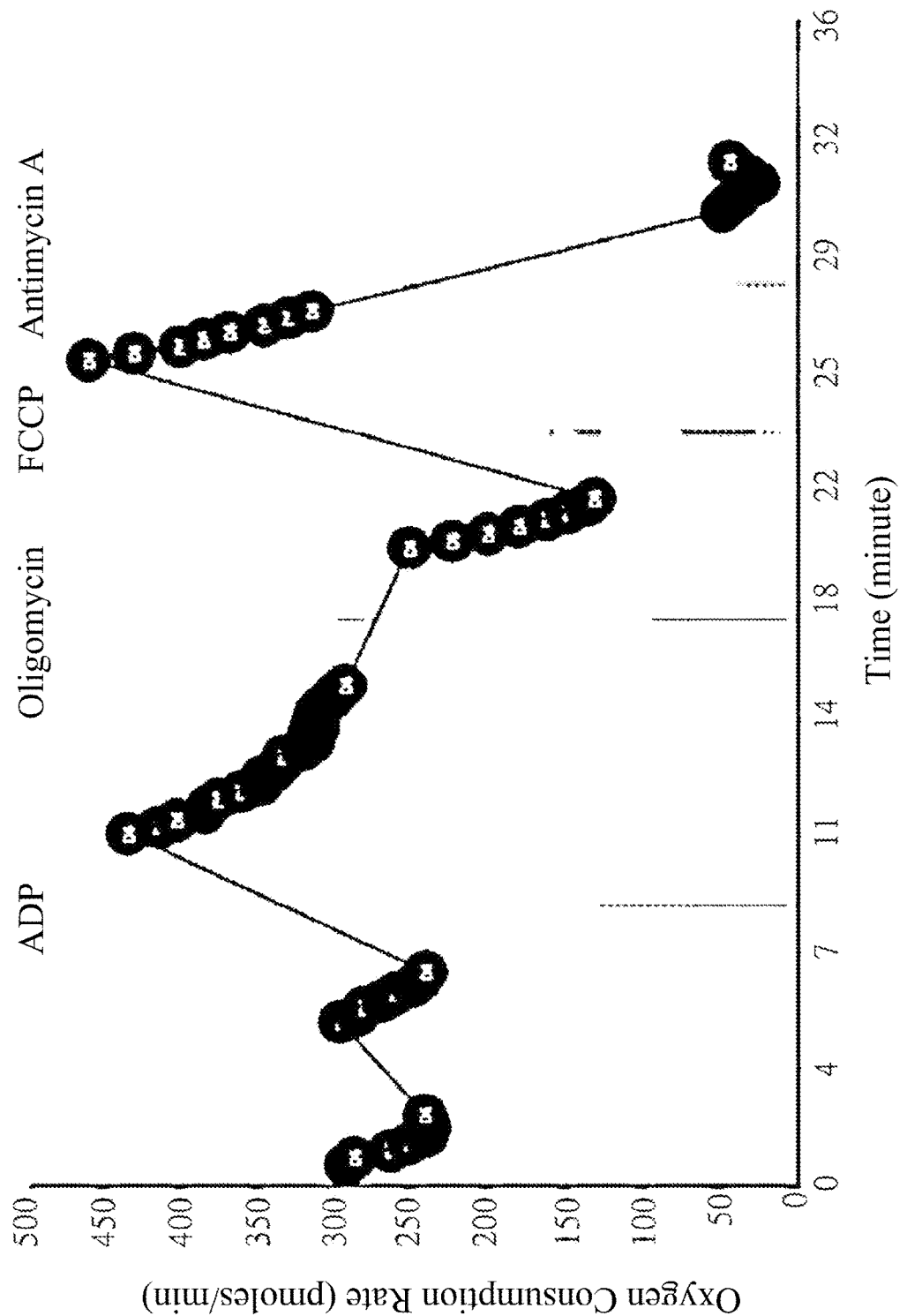
FIG. 1 shows the results of detecting activities of isolated mitochondria.
Figure 2A:
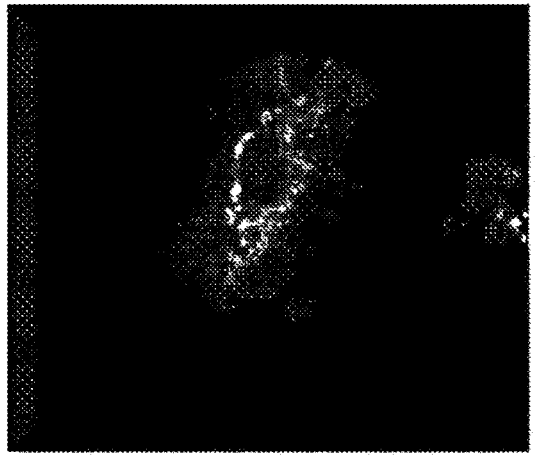
FIG. 2A shows a graph of immunofluorescence staining to observe exogenous mitochondria entering into human umbilical vein endothelial cells, in which the green fluorescence represents a signal stained with mitochondria antibody Ab-2.
Figure 2B:
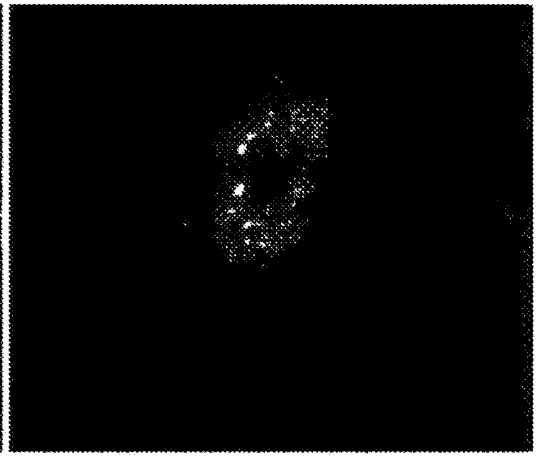
FIG. 2B shows a graph of immunofluorescence staining to observe exogenous mitochondria, which were stained with a mito-tracker of red fluorescence, entering into human umbilical vein endothelial cells after the exogenous mitochondria were co-cultured with the cells.
Figure 2C:
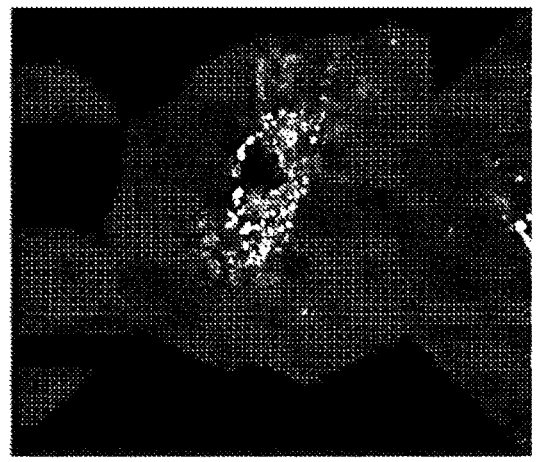
FIG. 2C shows the results of overlapping of FIGS. 2A and 2B.
Figure 2D:
FIG. 2D shows the human umbilical vein endothelial cells co-cultured with exogenous mitochondria observed with a bright-field microscope with the same field of view as FIGS. 2A and 2B.

Unless otherwise defined, the meanings of the technical and scientific terms used in the specification and claims of the present invention are the same as those generally understood by those skilled in the art to which this invention pertains. If there is any contradiction, the contents of the present invention shall prevail.

The term "isolated mitochondria" or "exogenous mitochondria" disclosed in the present invention refers to mitochondria isolated from a donor, a recipient, or a specific cell. Methods for isolating mitochondria are the separation and extraction techniques known to a person having ordinary skill in the art to which the claimed invention pertains. For example, mitochondria may be obtained by homogenizing the cells or tissues containing mitochondria and then centrifuging the homogenized cells or tissues.

The term "melatonin" disclosed in the present invention refers to a hormone presenting in a living organism and having the following formula (I):

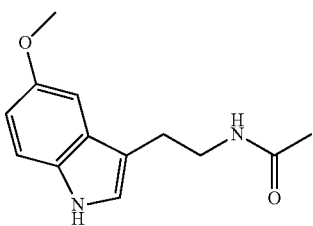

(I)

The term "rat model of acute respiratory distress syndrome" disclosed in the present invention has been shown to be successfully prepared by continuously exposing rats to pure oxygen (100% $O_2$) for 48 hours. Specifically, the results of previous studies show that rats that breathed pure oxygen for 53 hours died within 72 hours. In addition, rats that breathed pure oxygen for 48 hours survived after 72 hours, with arterial oxygen saturation ($SaO_2$) being less than 89% and the lungs having severe pulmonary parenchymal damage.

The term "western blot" or "western blotting" disclosed in the present invention refers to an immunoassay method for detecting the presence of proteins in a sample. The main steps of western blotting comprise separating proteins in a sample by SDS gel electrophoresis, transferring the separated protein onto a transfer membrane, such as a PVDF (polyvinylidene difluoride) membrane, immersing the transfer membrane in a blocking buffer and then in a solution containing primary antibodies against target proteins, and detecting the target proteins by secondary antibodies labeled with fluorescent dye.

The term "protein oxidation detection kit" disclosed in the present invention refers to methods for detecting protein oxidation in cells. For example, the Oxyblot Oxidized Protein Detection Kit S7150 (Chemicon) used in the examples of the present invention detects oxidized proteins by labeling oxidized proteins in a sample with 2,4-dinitrophenylhydrazine (DNPH), separating proteins in the sample with 12% SDS polyacrylamide gel electrophoresis, transferring the separated proteins onto a transfer membrane, such as a nitrocellulose membrane, immersing the transfer membrane in buffer containing anti-DNP primary antibody (1:150) for about 2 hours, then immersing the transfer membrane in buffer containing secondary antibody (1:300) at room temperature for about an hour, and then observing expression of oxidized proteins in the sample.

The term "an effective amount" disclosed in the present invention refers to the amount of the compound or active ingredient required to produce the desired effect, as indicated by weight percentages in the composition. As being appreciated by a person having ordinary skill in the art to which the claimed invention pertains, the effective amount varies depending on manners of administration that cause particular effects. In general, the amount of active ingredient or compound in the composition may be from about 1% to about 100%, preferably from about 30% to about 100% by weight of the composition.

The term "pharmaceutical composition" disclosed in the present invention refers to an effective amount of a desired compound or active ingredient to produce a particular effect, and at least one pharmaceutically acceptable carrier. As being appreciated by a person having ordinary skill in the art to which the claimed invention pertains, the type of pharmaceutical composition varies depending on manners of administration that cause particular effects, such as tablets, powders, injections, etc. In addition, the carrier may be solid, semi-solid, or liquid depending on the form of the pharmaceutical composition. For example, the carrier includes, but is not limited to, gelatin, emulsifier, hydrocarbon mixture, water, glycerol, physiological saline, buffered saline, lanolin, paraffin, beeswax, dimethyl silicone oil, and ethanol.

The term "administer," "administering," or "administration" disclosed in the present invention refers to a means of delivering a substance to a particular portion of a body, a particular cell, or a particular target, or a route where the substance is in contact with an individual. In general, the route of administration includes, but is not limited to, oral administration, dermal administration, spray, inhalation, and injection.

The term "a," "an," or "the" disclosed in the present invention is intended to cover one or more numerical values in the specification and claims unless otherwise specified.

The term "significant" or "significantly" in "significant difference," "significantly increase," or "significantly reduce" disclosed in the present invention indicates that there is a statistical difference between two sets of data after statistical analysis—that is p value <0.05. In the embodiments of the present invention, the so-called significant difference represents the p value <0.01.

In order to further explain the multi-effects of the present invention, it will be described in further detail with reference to the following examples. However, these examples are given for explanation, and the terms used in the examples do not limit the scope and the meaning of the specification and the claims of the present invention.

In addition, it must be specified that all animal testing in the examples was approved by the Kaohsiung Chang Gung Memorial Hospital Animal Care and Use Committee (Consent for Use of Animals No. 2008121108) and was conducted in accord with the Guide for the Care and Use of Laboratory Animals (National Institutes of Health Bulletin: 85-23, published by the National Academies Press, 1996).

All quantized data in the examples are presented in mean±standard deviation. Unless otherwise stated, the statistical method was ANOVA, and the analysis software was SAS (SAS Institute, Cary, N.C.).

Example 1: Preparation of Exogenous Mitochondria

Rats were sacrificed after being starved overnight, and their gallbladders and livers were removed. About 3 grams of the liver was immediately immersed in 50 ml of ice-cold IBc solution (10 mM Tris-MOPS, 5 mM EGTA/Tris, and 200 mM sucrose, pH 7.4), followed by washing the liver with ice-cold IBc solution to remove blood. The liver was shredded in a container surrounded by ice, the IBc solution for cleaning was removed, and 18 ml of new IBc solution was added. After the liver was homogenized, the homogenate was centrifuged at 600×g for 10 minutes at 4° C. The supernatant was removed and centrifuged at 7000×g for 10 minutes at 4° C., and the supernatant was then removed. The precipitate contained mitochondria isolated from the rat liver. The precipitate was suspended to obtain a mitochondrial suspension, and the concentration of the mitochondrial suspension was measured by Biuret test.

Each 10 mg of the isolated mitochondria was labeled with 1 µM mito-tracker with red fluorescence (MitoTracker Red CMXRos, Invitrogen, Carlsbad, Calif.) for later use in the subsequent examples.

Example 2: Detection of Activities of the Isolated Mitochondria

The mitochondrial suspension (10 µm) was diluted with cold 1× mitochondrial assay solution (MAS) and rotated at 3000×g for 30 min. The mitochondrial assay solution had a pH of 7.2 containing 70 mM sucrose, 220 mM mannitol, 10 mM potassium phosphate, 5 mM magnesium chloride, 2 mM HEPES, and 10 mM EGTA. The mitochondria were attached to a culture dish of an XF24 Extracellular Flux Analyzer (Seahorse Bioscience, MA, USA) and then tested for mitochondrial oxygen consumption rate by coupling, where the concentration of compound added at each stage of the coupling was as follows: 10 mM succinate, 0.5 mM ADP, 2 µM oligomycin, 4 µM FCCP, and 4 µM antimycin A.

The statistical results of the mitochondrial oxygen consumption rate are shown in FIG. 1.

As shown in FIG. 1, the electron transport chain and the oxidative phosphorylation in the mitochondria isolated from the rat liver were normal, which means the mitochondria had normal function.

Example 3: Assay of Exogenously Mitochondrial Transformation into Cells

Human umbilical vein endothelial cells ($5.0 \times 10^6$ cells) were co-incubated with 2 µM menadione for 30 minutes and then incubated with the labeled mitochondria at 37° C. for 30 minutes. Mitochondrial transformation into cells was observed by immunofluorescence staining and using transmission electron microscopy. The results are shown in FIG. 2 and FIG. 3.

Figures 3A, 3B:
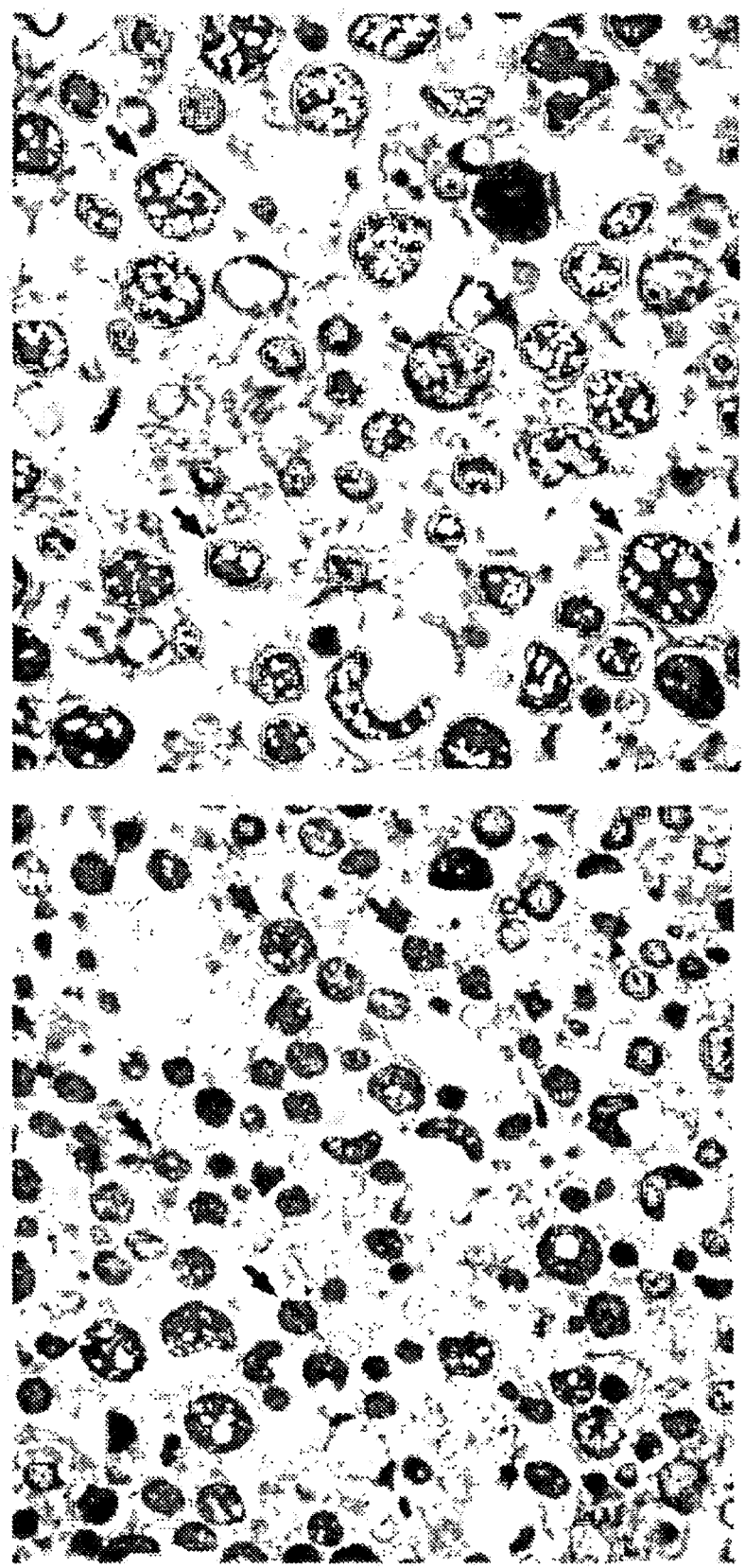
FIG. 3A shows the morphology of the isolated mitochondria observed with a transmission electron microscope at 12000× magnification. The arrow indicates an intact mitochondrion.
FIG. 3B shows the morphology of the isolated mitochondria observed with a transmission electron microscope at 25000× magnification. The arrow indicates an intact mitochondrion.

As shown in FIG. 2 and FIG. 3, a large number of mitochondria entered the human umbilical vein endothelial cells treated with menadione.

Example 4: Detection of Intracellular Protein Oxidation

Human umbilical vein endothelial cells were divided into three groups. The human umbilical vein endothelial cells of the first group remained untreated. The human umbilical vein endothelial cells of the second group were treated with menadione, and the human umbilical vein endothelial cells of the third group were treated with menadione and then exogenous mitochondrial. Protein oxidation in each group was detected after 0.5 hours and 6 hours of treatment with a commercially available protein oxidation assay kit (Oxyblot Oxidized Protein Detection Kit S7150, Chemicon), and oxidative stress in cells of each group was further analyzed with a software (Labwork software, UVP). The results are shown in FIG. 4.

Figures 4A, 4B:
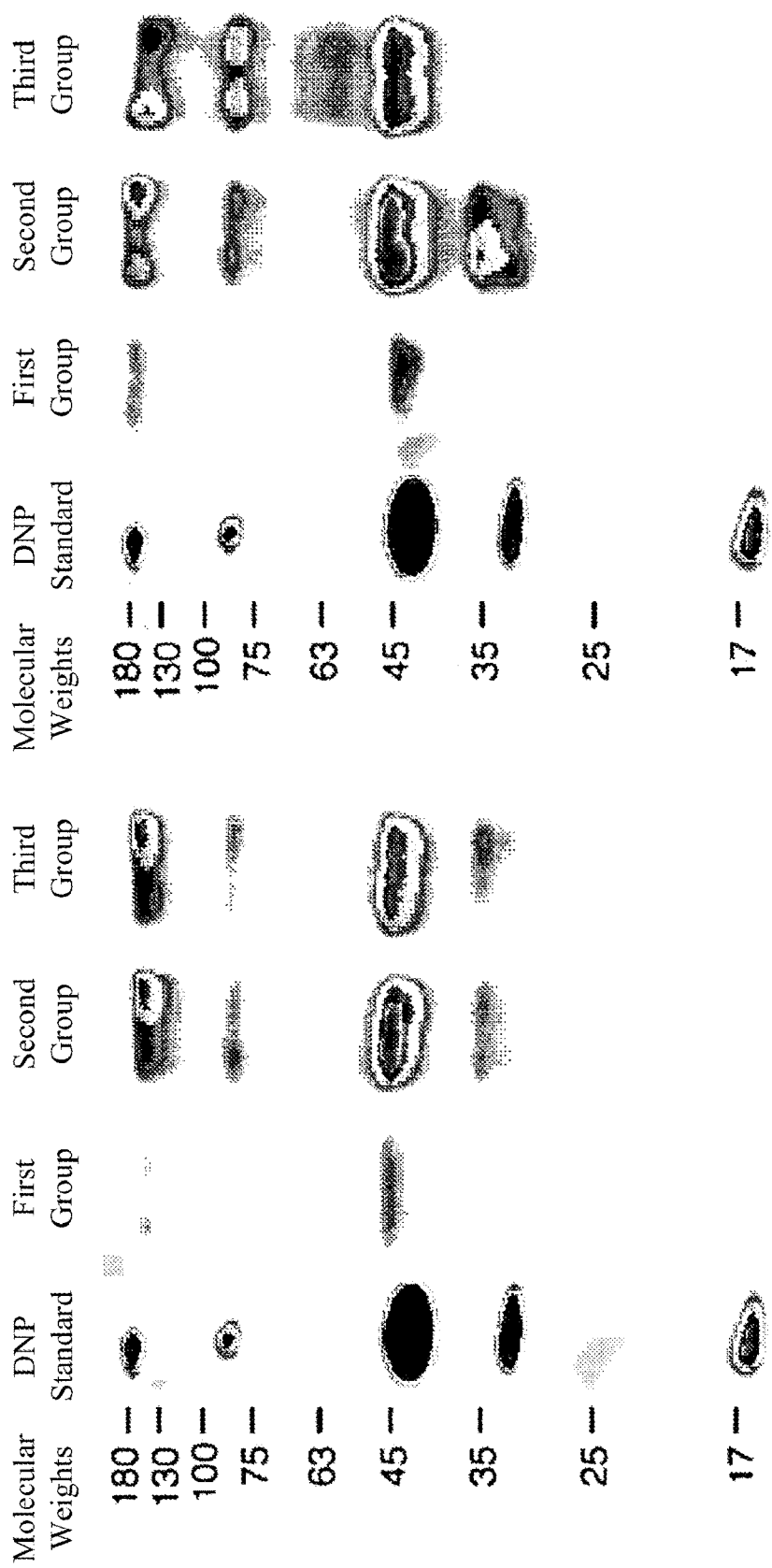
FIG. 4A shows detection of expression of oxidized proteins in each group after treatment under different conditions for 0.5 hour by western blotting.
FIG. 4B shows detection of expression of oxidized proteins in each group after treatment under different conditions for 6 hours by western blotting.
Figure 4C:
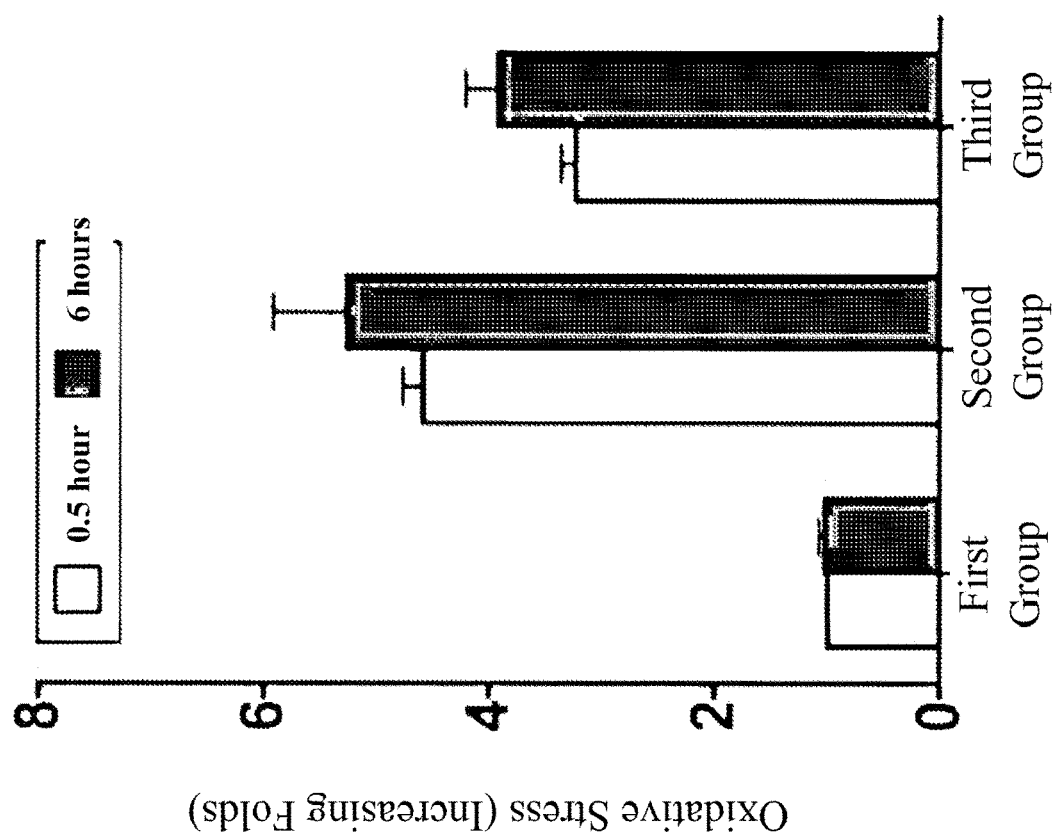
FIG. 4C shows the quantification results of FIGS. 4A and 4B.

Since menadione-induced oxidative stress in cells causes cell damage, the results shown in FIG. 4 indicate that, protein oxidation increased significantly in the human umbilical vein endothelial cells of the second group under oxidative stress, compared to protein oxidation in the cells of the first group. In addition, although the human umbilical vein endothelial cells of the third group were under oxidative stress as well, protein oxidation in the cells of the third group decreased significantly compared to that in cells of the second group. Accordingly, transformation of exogenous mitochondria with normal function into cells is able to protect cells from damages caused by oxidative stress.

Accordingly, the pharmaceutical compositions containing mitochondria disclosed in the present invention are capable of protecting cells from injury induced by oxidative stress.

Example 5: Animal Grouping

A total of forty (40) specific pathogen free (SPF) adult male SD rats, each weighing 350-400 g (Charles River Technology, BioLASCO Biotechnology Co., Ltd., Taiwan) were used in the examples. The SD rats were randomly divided into 5 groups: the first group was the normal control group; the second group was the rat model of acute respiratory distress syndrome; the third group was the rat model of acute respiratory distress syndrome intraperitoneally injected with melatonin, with each dose of 50 mg per kilogram, at the 6th and the 24th hour after breathing pure oxygen; the fourth group was the rat model of acute respiratory distress syndrome intravenously injected mitochondria, with a dose of 1500 µg per rat, at the 6th hour after breathing pure oxygen; the fifth group was the rat model of acute respiratory distress syndrome administered melatonin and mitochondria in the same manners, frequency, and doses as those of the third group and the fourth group, respectively.

Example 6: Results of Hemodynamics Test for Rats in Each Group

Rats in each group in Example 5 were anesthetized. Arterial blood was taken from the carotid arteries of rats in each group, and the oxygen saturation of the blood samples was analyzed. The results are shown in FIG. 5.

Then, rats in each group were provided air with positive pressure ventilation (180 ml per minute) using small animal ventilators (SAR-830/A, CWE, Inc., USA) and intubation. Left thoracotomy was performed on rats in each group, and soft plastic needles were inserted into the right ventricle of rats in each group. Signals of right ventricular systolic pressure were measured with a pressure transducer (UFI, model 1050, CA, USA) and transmitted to bridge amplifiers (ML866 PowerLab 4/30 Data Acquisition Systems. ADInstruments Pty Ltd., Castle Hill, NSW, Australia) to obtain the right ventricular systolic pressure of rats in each group as a reference for pulmonary hypertension. In addition, femoral artery systolic blood pressure of rats in each group was measured. The right ventricular systolic pressure and the femoral artery systolic blood pressure were analyzed by software (Labchart, ADInstrument). The results are shown in FIG. 6 and FIG. 7.

Figure 9:
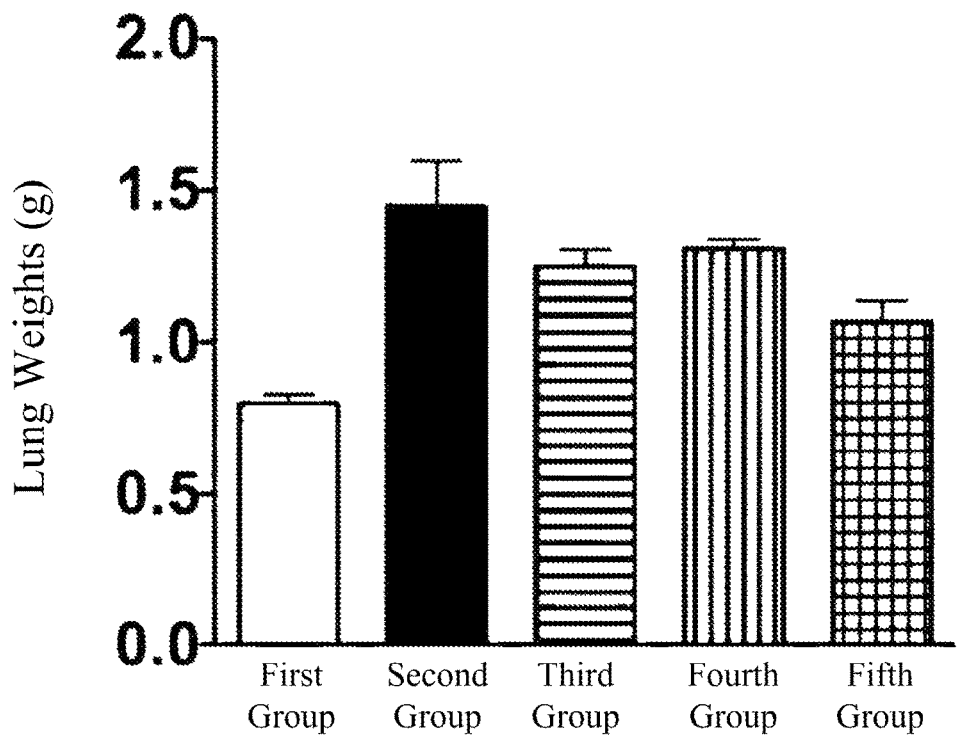
FIG. 9 shows the results of measuring weights of the lungs of rats in each group.
Figure 10:
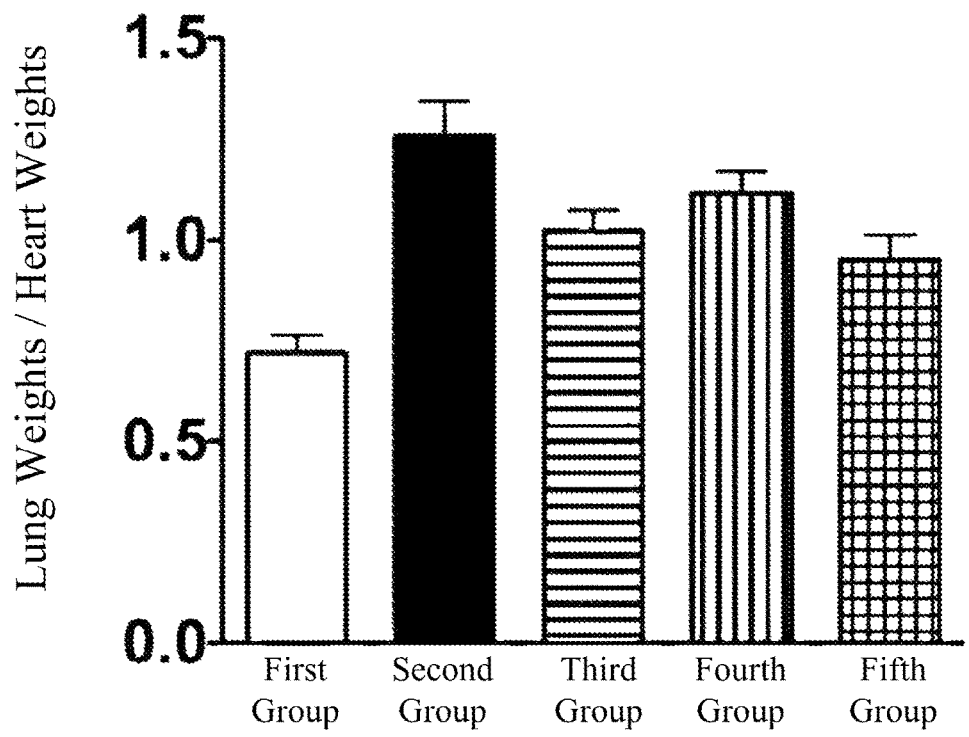
FIG. 10 shows the ratio of lung weight to heart weight of rats in each group.

After that, rats in each group were sacrificed, and the hearts and lungs were taken for weighing. The results are shown in FIG. 8 to FIG. 10.

Figure 5:
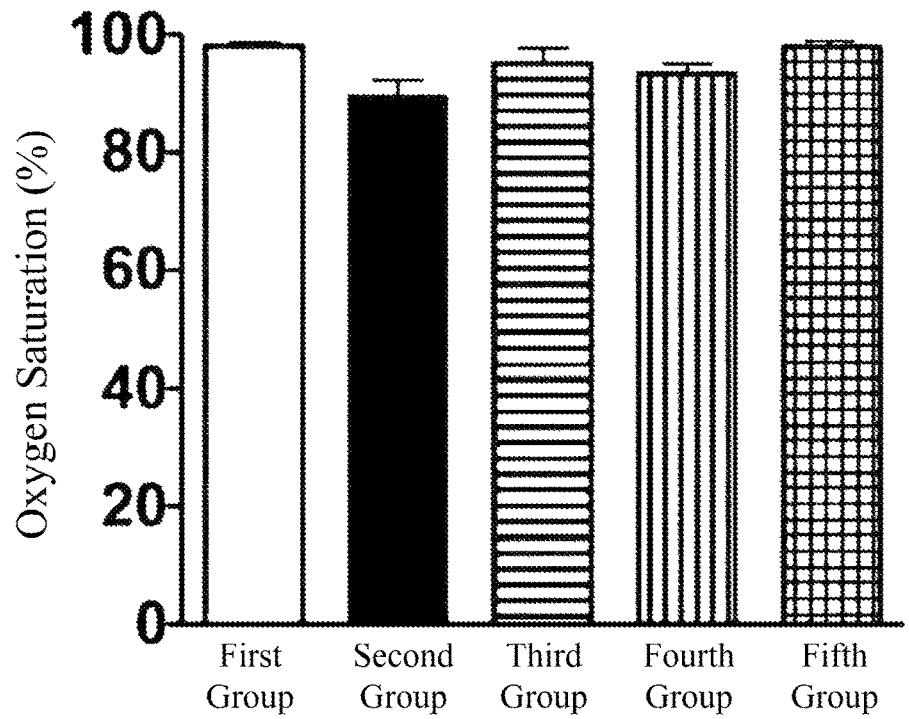
FIG. 5 shows the results of analyzing the oxygen saturation of each group.

As shown in FIG. 5, rats in the first group had the highest oxygen saturation, whereas rats in the second group had the lowest oxygen saturation. The oxygen saturation of the third group was significantly higher than that of the fourth group. The blood oxygen saturation of the fifth group was significantly higher than that of the third and fourth groups, and there was no significant difference between the first group and the fifth group.

Figure 6:
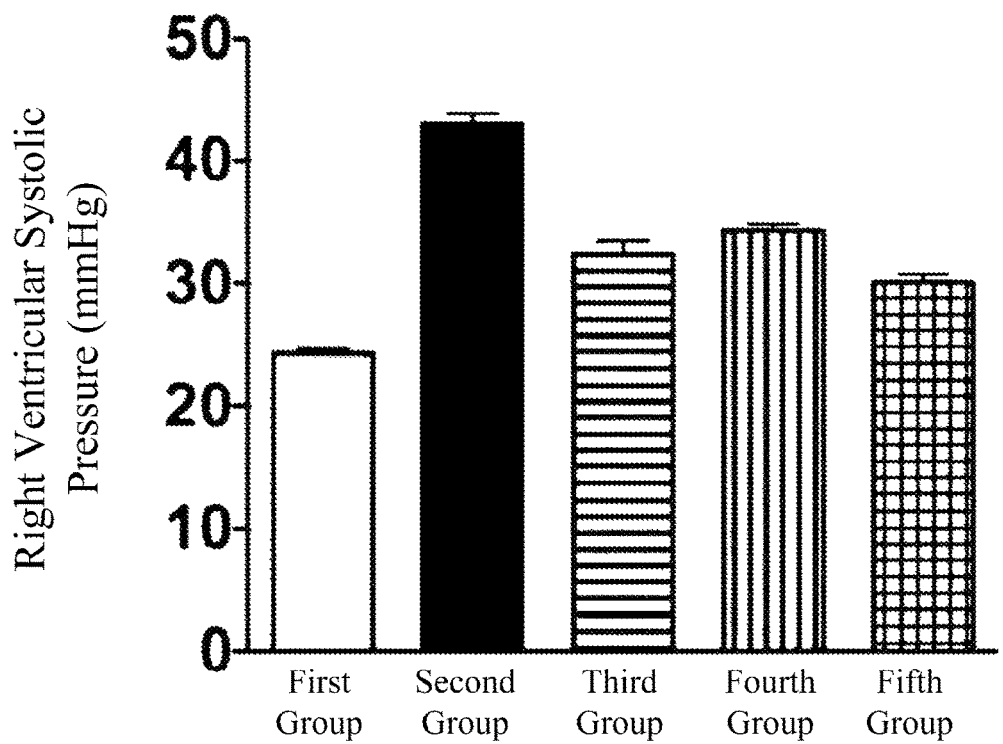
FIG. 6 shows the results of measuring right ventricular systolic pressure of rats in each group.
Figure 7:
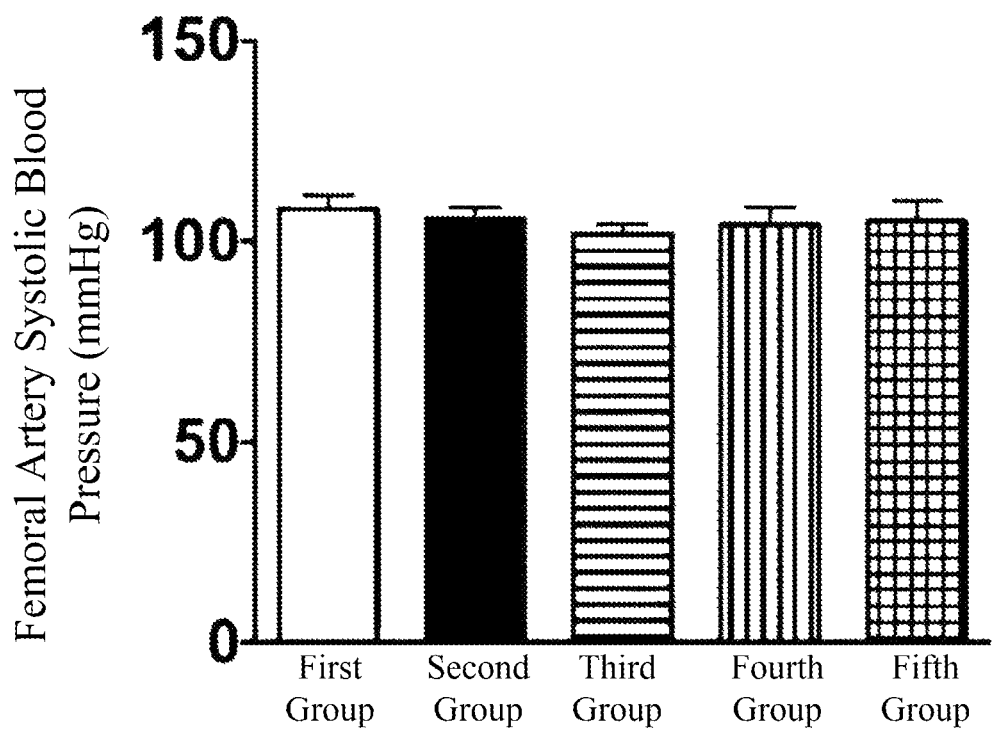
FIG. 7 shows the results of measuring systolic blood pressure in femoral arteries of rats in each group.

As shown in FIG. 6, rats in the first group had the lowest right ventricular systolic pressure, whereas rats in the second group had the highest right ventricular systolic pressure. Compared with the fourth group, the right ventricular systolic pressure was significantly reduced in the third group. The right ventricular systolic pressure of the fifth group was significantly lower than that of the third and fourth groups. As shown in FIG. 7, there was no significant difference in femoral artery systolic blood pressure among the first to the fifth groups.

Figure 8:
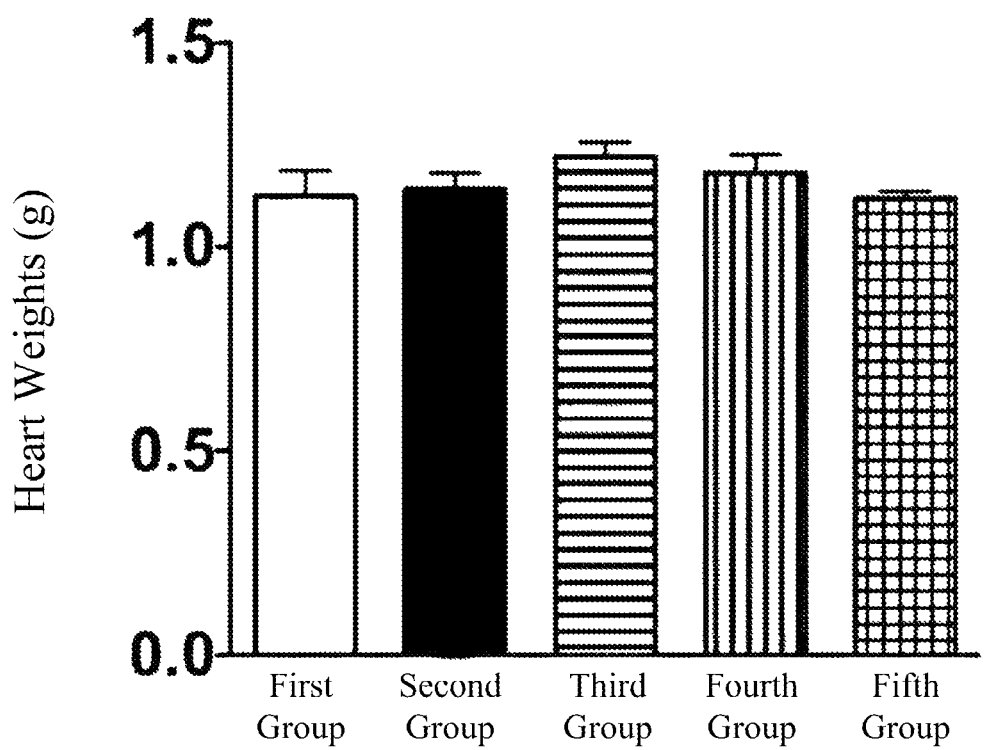
FIG. 8 shows the results of measuring weights of the hearts of rats in each group.

Please refer to FIG. 8, showing that the weights of the heart tissue in each group are similar. However, there is a negative correlation between the results of comparing the oxygen saturation of the five groups (see FIG. 5) and the results of comparing the weights of lung tissue (see FIG. 9) and lung weights to heart weights (see FIG. 10). Furthermore, there is a positive correlation between the weights of lung tissue (see FIG. 9) and the right ventricular systolic pressure (see FIG. 6).

Based on the results above, it was found that continuous administration of pure oxygen to an individual for 72 hours resulted in lung injury, a decrease in oxygen saturation, and an increase in right ventricular systolic pressure. By administering an effective amount of mitochondria or a composition containing mitochondria and melatonin to the individual, oxygen saturation can be increased effectively, and right ventricular systolic pressure can be reduced effectively. Among all these treatments, administering compositions containing exogenous mitochondria and melatonin had the best effects.

Accordingly, the pharmaceutical compositions of the present invention are capable of treating lung injury, respiratory distress syndrome and/or related symptoms thereof.

Example 7: Detection of BAL Fluid of Rats in Each Group

Figure 11A:
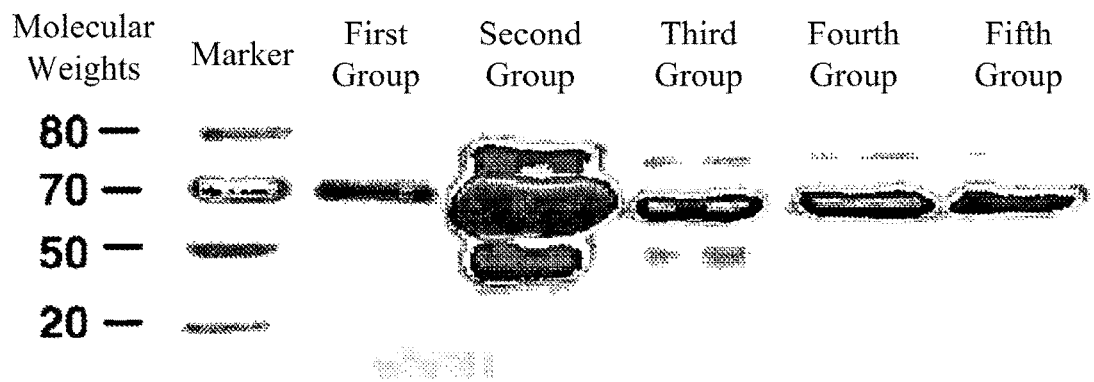
FIG. 11A shows the albumin levels in the BAL fluid of rats in each group detected by SDS gel electrophoresis.
Figure 11B:
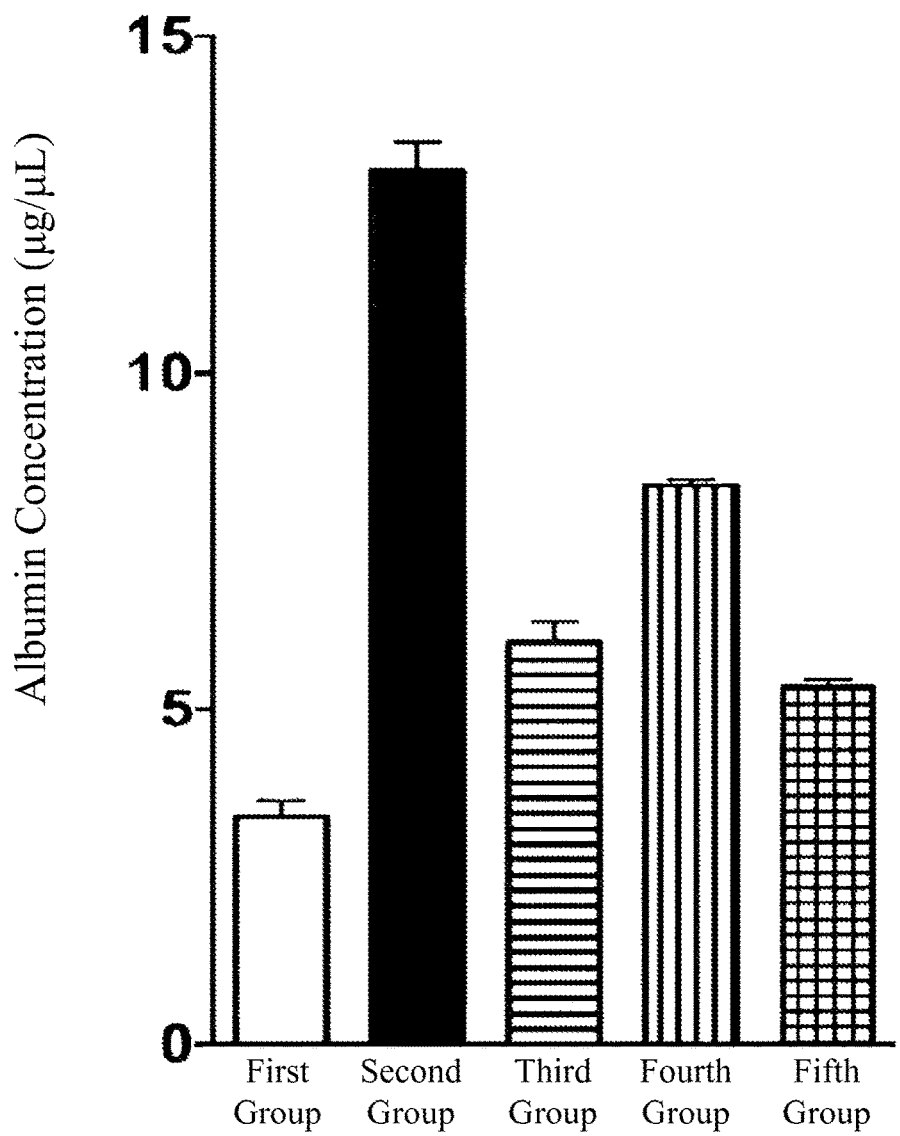
FIG. 11B shows the concentration of albumin in the BAL fluid of rats in each group.
Figure 12:
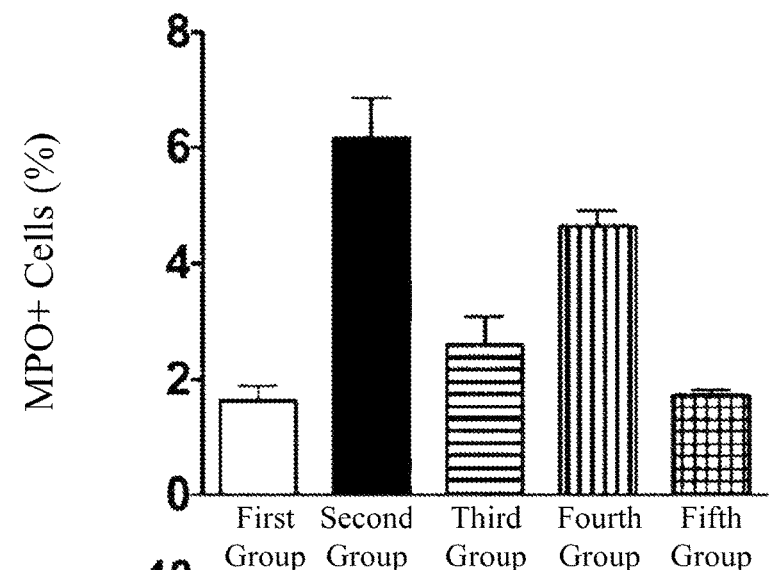
FIG. 12 shows the ratio of MPO+ cells in the BAL fluid of rats in each group.
Figure 13:
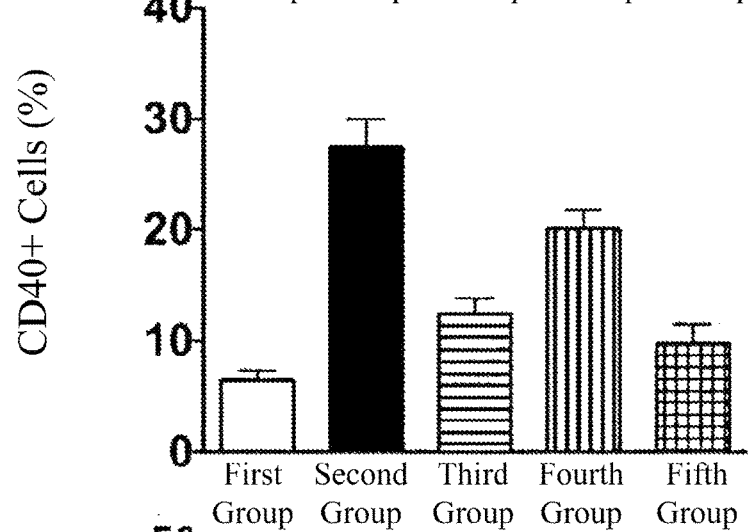
FIG. 13 shows the ratio of CD40+ cells in the BAL fluid of rats in each group.
Figure 14:
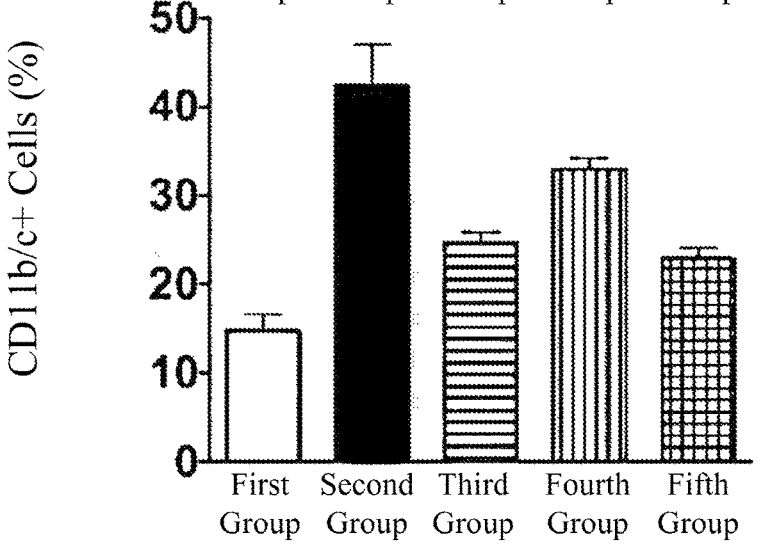
FIG. 14 shows the ratio of CD11b/c+ cells in BAL fluid of rats in each group.
Figure 15A:
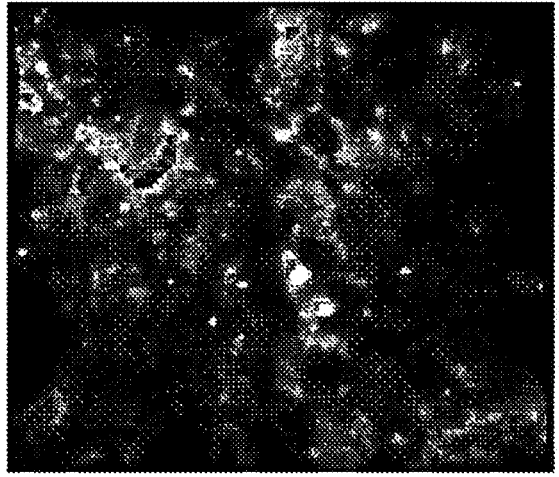
FIG. 15A shows a graph of immunofluorescence staining to observe mitochondria entering lung parenchyma of rats of the third group, in which the green fluorescence represents a signal stained with mitochondria antibody Ab-2.
Figure 15B:
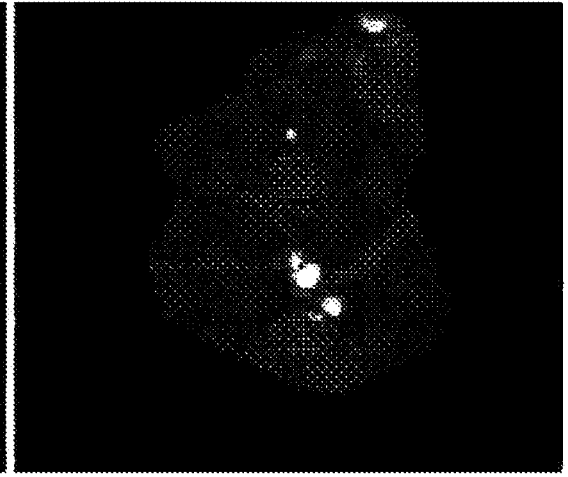
FIG. 15B shows a graph of immunofluorescence staining to observe mitochondria entering lung parenchyma of rats of the third group, in which the red fluorescence represents a signal stained with mito-tracker.
Figure 15C:
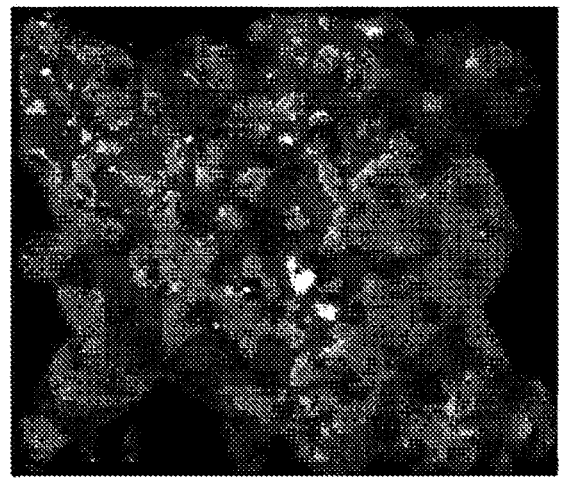
FIG. 15C shows the results of overlapping of FIGS. 15A and 15B.
Figure 15D:
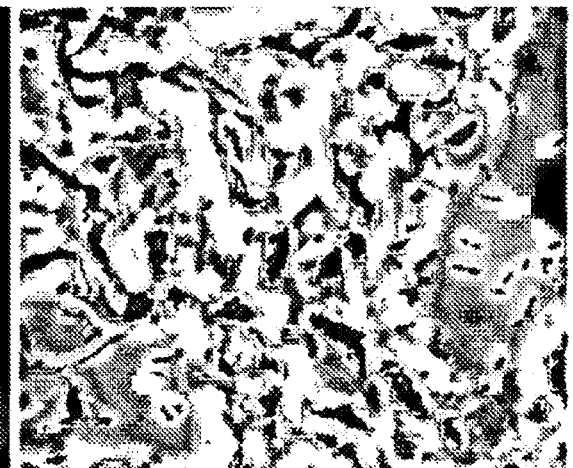
FIG. 15D shows the morphology of the lung tissues observed with visible light with the same field of view as FIGS. 15A, 15B, and 15C.

BAL fluid was obtained from rats in each group by bronchoalveolar lavage (BAL). SDS-PAGE and Coomassie Blue staining were used to detect the concentration of albumin in the BAL fluid of each group, and the results are shown in FIG. 11. Furthermore, the number of MPO+, CD40+, and CD11b/c+ cells in the BAL fluid of each group was calculated by flow cytometry. The results of the statistical analysis are shown in FIG. 12 to FIG. 14.

As shown in FIG. 11 to FIG. 14, the albumin concentration and the number of inflammatory cells in the first group were the lowest among the five groups, whereas the albumin concentration and the number of inflammatory cells in the second group were the highest among the five groups. The albumin concentration and the number of inflammatory cells in the fifth group were significantly lower than those in the second and fourth groups, and the albumin concentration and the number of inflammatory cells in the third group were significantly lower than those in the second group.

Based on the results in which the albumin concentration and the number of inflammatory cells in the second group increased significantly, continuous administration of pure oxygen to an individual for 72 hours induced symptoms of acute lung injury and caused pneumonia. However, by administering mitochondria or compositions containing mitochondria and melatonin to individuals with symptoms of acute lung injury, the albumin concentration and the number of inflammatory cells in the BAL fluid can be decreased effectively. Among all these treatments, administering compositions containing exogenous mitochondria and melatonin had the best effects.

Accordingly, the pharmaceutical compositions disclosed herein are capable of treating or ameliorating symptoms of acute lung injury or pneumonia.

Example 8: Observation of Lung Tissue Sections of Rats in Each Group

The left lungs of rats in each group were inflated with constant airway pressure (15-20 mmHg) and embedded with OCT (Tissue-Tek) for immunohistochemical staining. The right lungs of rats in each group were fixed with 4% paraformaldehyde and 0.1% glutaraldehyde phosphate buffer solution, then embedded in paraffin, and stained with hematoxylin and eosin.

Figure 16A:
FIGS. 16A to 16C show the images of lung tissue sections of rats of the first to third groups observed with a transmission electron microscope, respectively, in which the arrows indicate mitochondria.
Figure 16B:
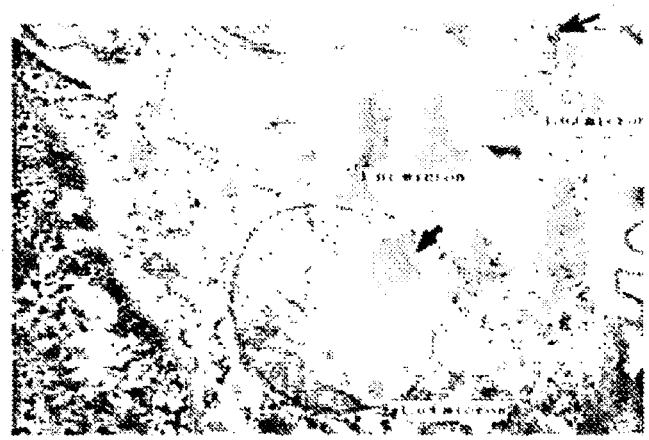
Figure 16C:

The results of immunofluorescence staining of lung slices of rats were observed with a confocal microscope. As shown in FIG. 15, green represents mitochondria stained with mitochondrial antibody 2 in lung tissue, and red represents exogenous mitochondria stained with the red fluorescent of mito-tracker. Furthermore, the lung sections of the first group, the second group, and the third group were observed with a transmission electron microscope. The results are shown in FIG. 16, where the arrow indicates mitochondria.

The lung tissue sections of rats in each group stained with hematoxylin and eosin were observed at a magnification of 100×. The results are shown in FIGS. 17A to 17E. Furthermore, three lung sections of one rat in each group were selected, and three high power fields (HPFs; 100×) were randomly selected from each of the sections to calculate the number of alveolar sacs of each group in the high magnification fields. The total number of alveolar sacs was divided by 9 to obtain the average number of alveolar sacs of each group in the high magnification fields. The results are shown in FIG. 18.

Figure 19:
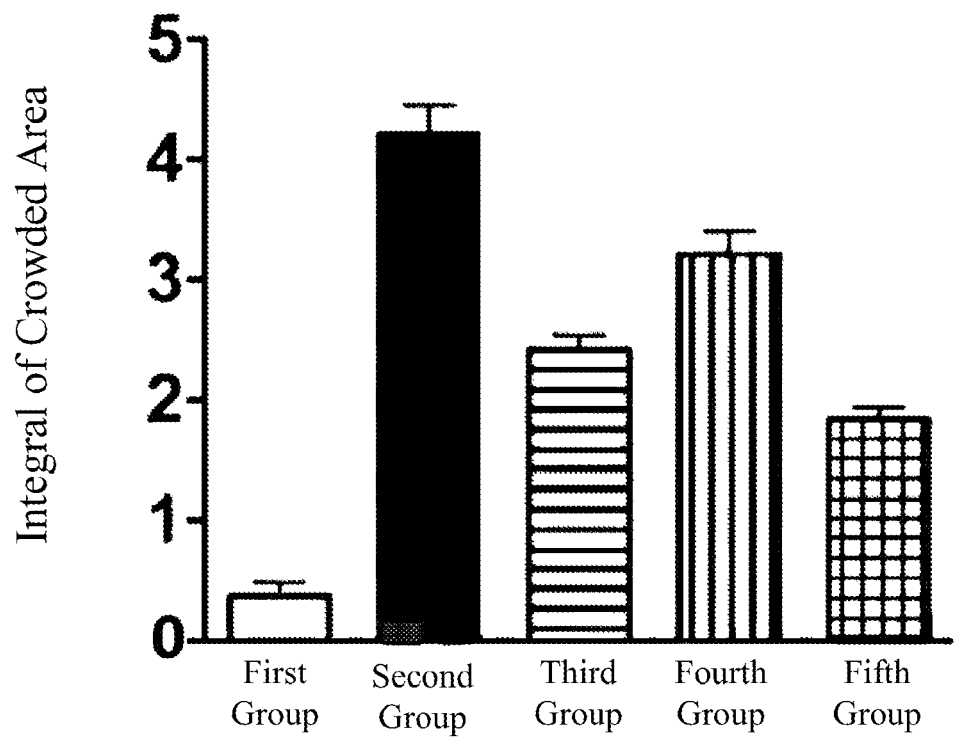
FIG. 19 shows the statistical results of the crowded area of the lung parenchyma of rats in each group by integration.

The integral of the crowded area in the lung tissue of rats in each group was further calculated by the following criteria: 0 represents no overlap; 1 represents less than 15% of crowded area in each of the high magnification fields; 2 represents 15-25% of crowded area in each of the high magnification fields; 3 represents 25-50% of crowded area in each of the high magnification fields; 4 represents 50-75% of crowded area in each of the high magnification fields; 5 represents 75-100% of crowded area in each of the high magnification fields. The so-called crowded area refers to the thickened interval in lung parenchyma, which is associated with partial or complete collapse of alveoli. The integral of the crowded area in the lung tissue of rats in each group is shown in FIG. 19.

As shown in FIG. 15, exogenous mitochondria did enter the alveolar epithelium of rats with acute respiratory distress syndrome. As shown in FIG. 16, the sizes of mitochondria of rats in the second group increased compared with those of rats in the first group, and there are few cristae in the mitochondrial inner membranes of rats in the second group. Compared with those of rats in the second group, the sizes of mitochondria of rats in the third group are smaller, and there are cristae in the mitochondrial inner membranes.

Figure 18:
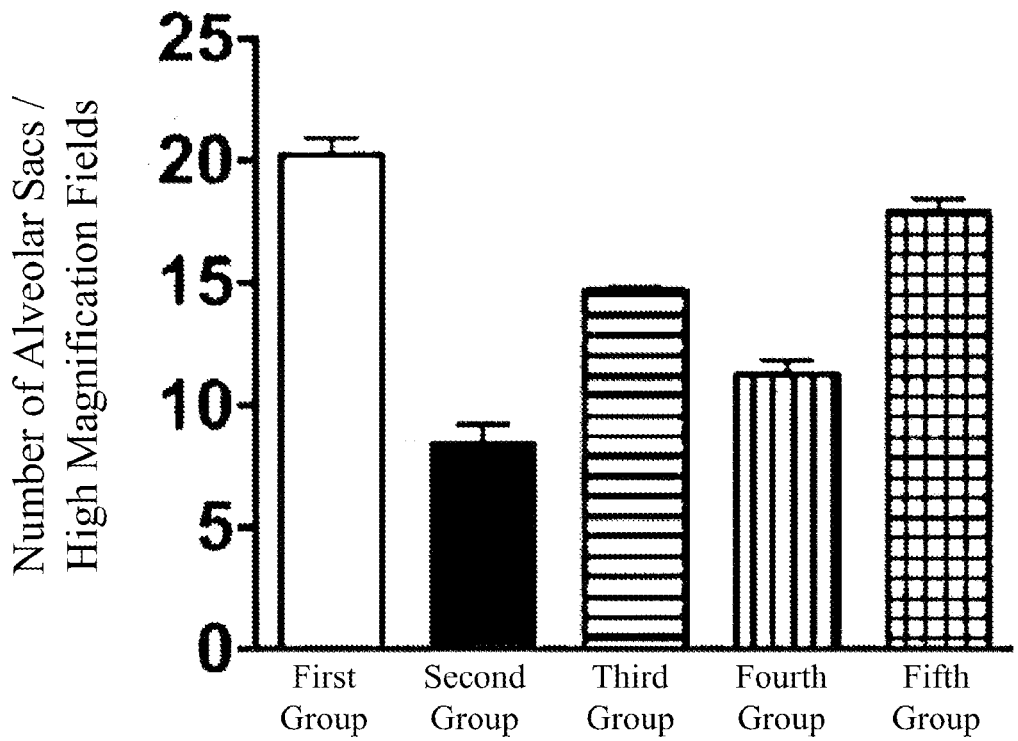
FIG. 18 shows the statistical results of the number of alveolar sacs of rats in each group.

As shown in FIG. 17 and FIG. 18, the number of alveolar sacs in the first group was the highest, and the number of alveolar sacs in the second group was the least. The number of alveolar sacs in the fifth group was significantly higher than that in the third and fourth groups, and the number of alveolar sacs in the third group was significantly higher than that in the second group. As shown in FIG. 19, there was almost no crowded area in the lung tissue of rats in the first group, and the integral was the lowest. The crowded area in the lung tissue of the second group was the highest. The crowded area in the lung tissue of the fifth group was significantly lower than that of the third group and the fourth group, and the crowded area in the lung tissue of the fourth group was significantly lower than that of the second group. Comparing FIG. 18 with FIG. 19, it was found that the two results showed a negative correlation.

From the above results, rat model of acute respiratory distress syndrome had swollen and deformed mitochondria and atelectasis, which lead to severe lung injury. However, by administering exogenous mitochondria with normal function or compositions containing exogenous mitochondria and melatonin to individuals with severe lung injury to allow the exogenous mitochondria to enter the alveoli, it can improve the mitochondrial morphology, restore the mitochondrial function, and reduce the collapse of the lungs. Among all these treatments, administering compositions containing exogenous mitochondria and melatonin had the best effects.

Therefore, the pharmaceutical compositions disclosed herein have the effect of treating or ameliorating severe lung injury and/or related symptoms.

Example 9: Detection of Inflammatory Cells and Antioxidant Biomarkers in Rats of Each Group The paraffin sections of the lung tissue of each group were rehydrated with 3% hydrogen peroxide for 30 minutes, followed by the addition of a high-performance Immuno-Block reagent (BioSB) at room temperature for 30 minutes. The sections were then treated with the specific primary antibody of the following proteins, respectively: F4/80 (1:100, Abcam), γ-H2AX (1:500, Abcam), heme oxygenase-1 (HO-1; 1:2000, Abcam), and Cx43. Immunohistochemical staining was performed on the sections of the lung tissue of each group to observe the expression of F4/80, γ-H2AX, heme oxygenase-1, and Cx43 in cells. In addition, the expression of the proteins mentioned above in the lung tissue sections of each group was quantified, and the results are shown in FIG. 20 to FIG. 23. The red fluorescence represents the exogenous mitochondria labeled by mitotracker, and the green fluorescent represents the mitochondria within the lungs.

The data were quantified as follows. Three lung sections of one rat in each group were selected for immunofluorescence staining, and then three high power fields (HPFs; 400×) were randomly selected from each of the sections to calculate the number of positive staining cells of each group in the high magnification fields. The total number of positive staining cells was divided by 9 to obtain the average number of positive staining cells of each group in the high magnification fields.

Figure 20F:
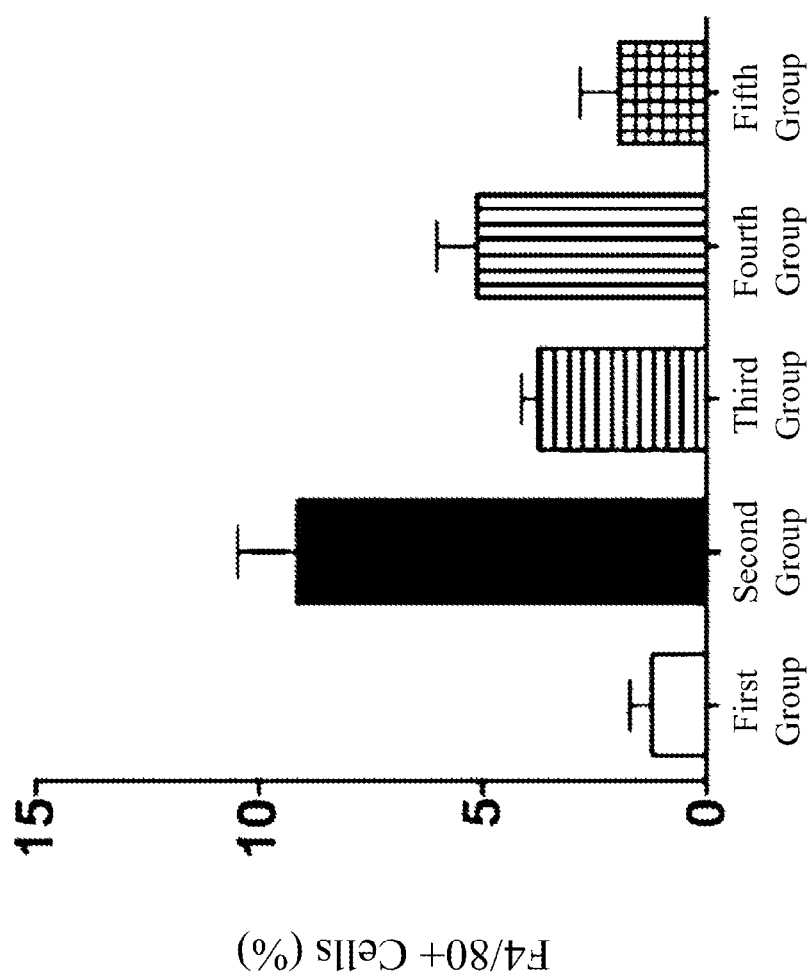
FIG. 20F shows the quantification results of cells expressing F4/80 in the lung tissue sections of rats in each group.
Figure 21F:
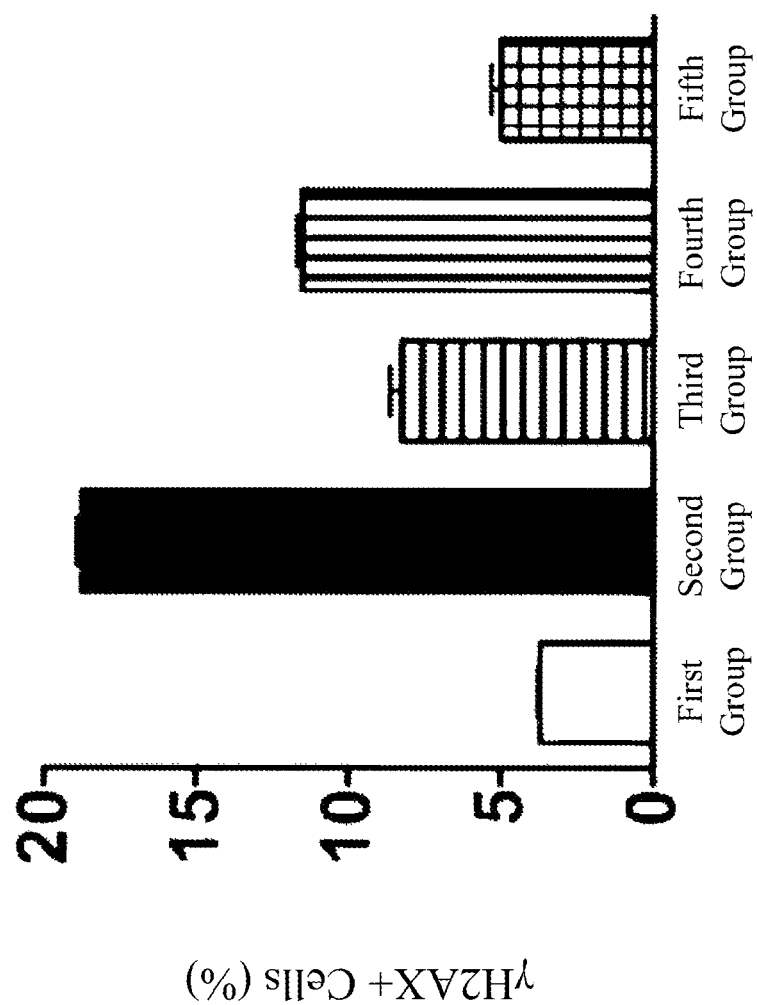
FIG. 21F shows the quantification results of cells expressing γ-H2AX in the lung tissue sections of rats in each group.

Please refer to FIG. 20 and FIG. 21, for expression of F4/80 and γ-H2AX, the first group was the lowest among the five groups, the second group was the highest among the five groups, and the fifth group was significantly lower then the third group and the fourth group, in which the third group was significantly lower than the fourth group.

Figure 22F:
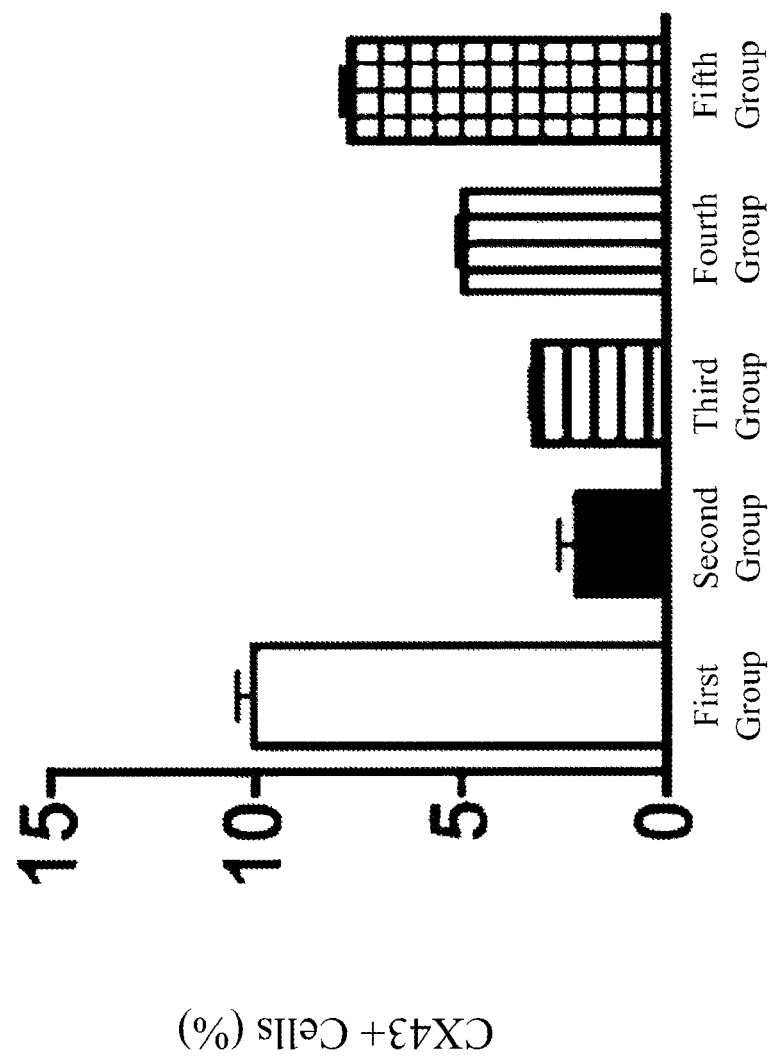
FIG. 22F shows the quantification results of cells expressing Cx43 in the lung tissue sections of rats in each group.

Please refer to FIG. 22, for expression of Cx43, the first group was the highest among the five groups, the second group was the lowest among the five groups, and the fifth group was significantly higher then the third group and the fourth group, in which the fourth group was significantly higher than the third group.

Figure 23F:
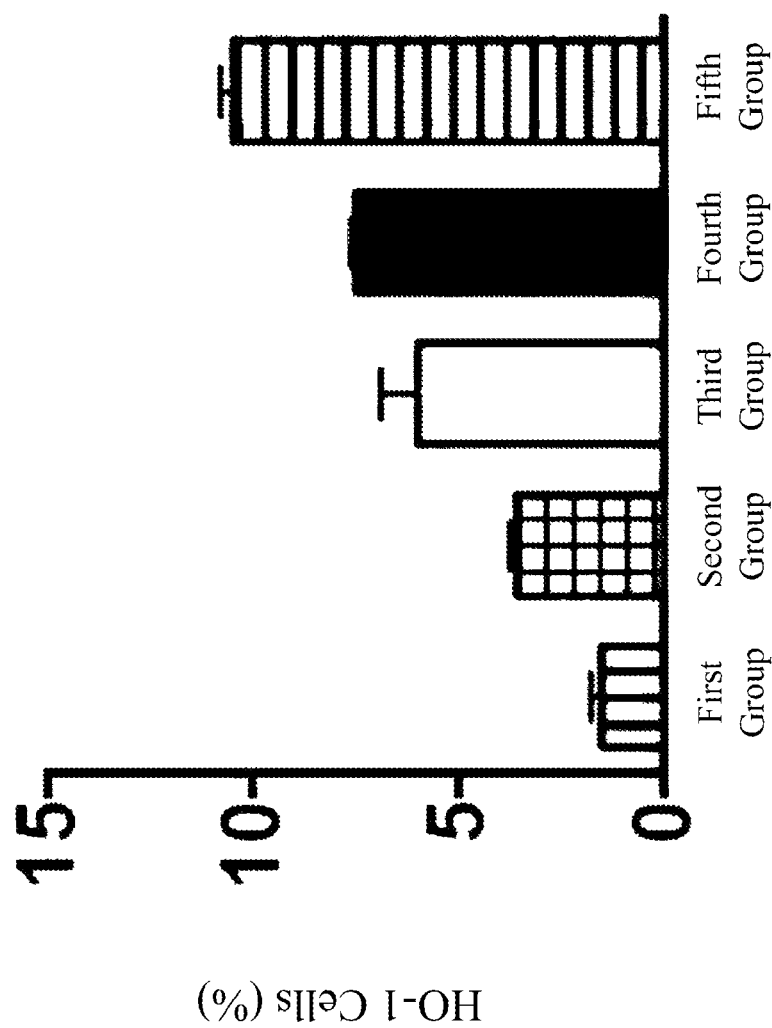
FIG. 23F shows the quantification results of cells expressing heme oxygenase-1 (HO-1) in the lung tissue sections of rats in each group.

Please refer to FIG. 23, for expression of heme oxygenase-1, the fifth group was the highest among the five groups, the first group was the lowest among the five groups, and the third group was significantly higher then the second group.

Based on the previous studies, F4/80 is a specific marker on the surface of macrophages and is used as an marker of intracellular inflammatory response; γ-H2AX is a marker of DNA damage; Cx43 is a gap junction protein whose expression is related to alveoli and permeability of microvascular on alveoli; heme oxygenase-1 is a biomarker for antioxidant capacity and is used as an indicator for assessing lung protection. Therefore, the results of FIG. 20 to FIG. 23 show that continuous administration of pure oxygen to an individual caused cellular DNA damage, affected the normal physiological function of lung cells, increased the number of inflammatory cells in pulmonary parenchyma of the individual, and reduced the alveolar permeability. Exogenous mitochondria or compositions containing mitochondria and melatonin is an antioxidant capable of counteracting the heme oxygenase-1 produced by damaged lung tissues and reducing damage and inflammation of cells caused by oxidative stress to maintain normal physiological function of lung cells. Among all these treatments, administering compositions containing mitochondria and melatonin had the best effects.

Accordingly, the pharmaceutical compositions disclosed herein are an antioxidant effectively against lung injury and can be used for treating or ameliorating acute respiratory distress and/or related symptoms.

Example 10: Detection of the Expression of Proteins Associated with Inflammation, Oxidative Stress, Fibrosis, and Apoptosis in the Lung Parenchyma of Each Group The protein extracts of the left lungs of rats in each group were prepared. The same amount (10 to 30 μg) of protein extracts of rats in each group was detected by western blotting and Oxyblot Oxidized Protein Detection Kit S7150, Chemicon, respectively. The results were observed by enhanced chemiluminescence (ECL, Amersham Biosciences), and the performance of each protein was quantified by software (Labwork software, UVP). The results are shown in FIGS. 24 to 42.

Specifically, the procedure and conditions of western blotting were as follows: Proteins were separated by SDS gel electrophoresis with a gradient of 8-10% polyacrylamide solution. The blocking agent used was a T-TBS solution containing 5% skimmed milk powder and 0.05% Tween. Primary antibodies were against the following proteins respectively: NOX-1 (1:1500, Sigma), NOX-2 (1:750, Sigma), NOX-4 (1:1000, Abcam), or interacted with polyclonal antibodies that were against the following proteins: tumor necrosis factor α (1:1000, Cell Signaling), nuclear factor κB (1:250, Abcam), matrix metalloproteinase 9 (1:3000, Abcam), transforming growth factor β (1:1000, Abcam), Smad3 (1:500, Cell Signaling), bone morphogenetic protein-2 (1:100, Abcam), Smad 1/5 (1:500, Cell Signaling), GR (1:1000, Abcam), GPx (1:1000, Abcam), Cytochrome C (1:2000, BD), NQO 1 (NAD(P)H: quinone oxidoreductase 1; 1:1000, Abcam), Heme oxygenase-1 (1:250, Abcam), caspases 3 (1:1000, Cell Signaling), and PARP (poly (ADP-ribose) polymerase; 1:1000, Cell Signaling). Secondary antibodies conjugated to HRP enzymatic fluorescence are goat antibody against mouse IgG, goat antibody against rat IgG, or goat antibody against rabbit IgG.

Figure 24A:
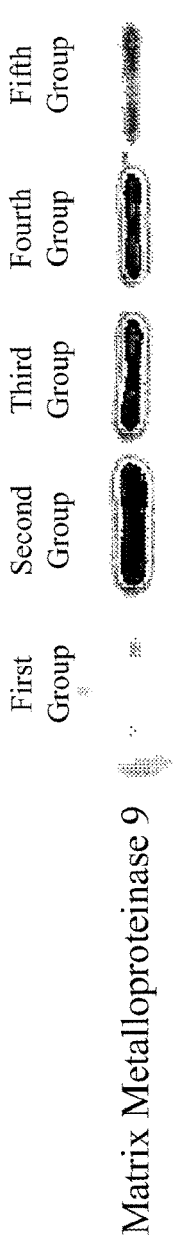
FIG. 24A shows the expression of matrix metalloproteinase-9 in lung cells of rats in each group detected by western blotting.
Figure 24B:
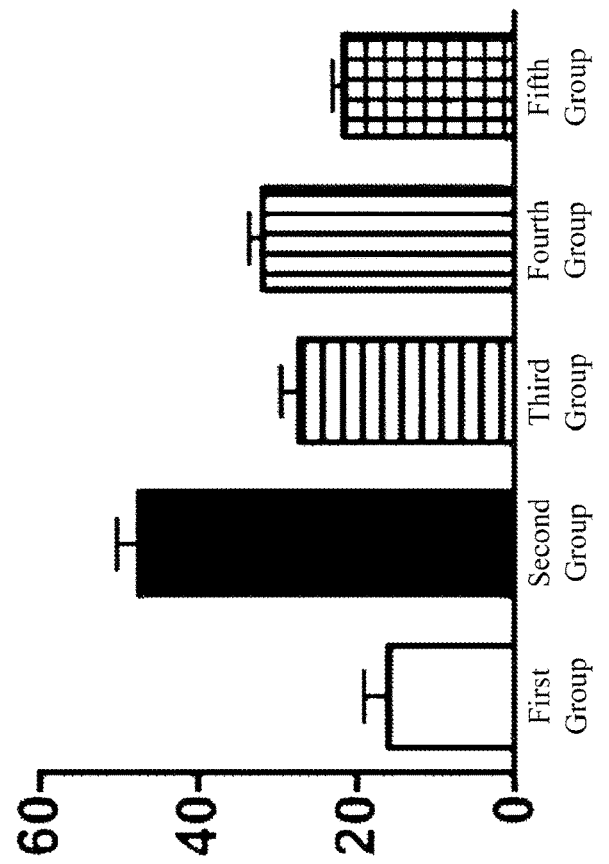
FIG. 24B shows the quantification results of the expression of matrix metalloproteinase-9 of rats in each group in FIG. 24A.
Figure 25A:
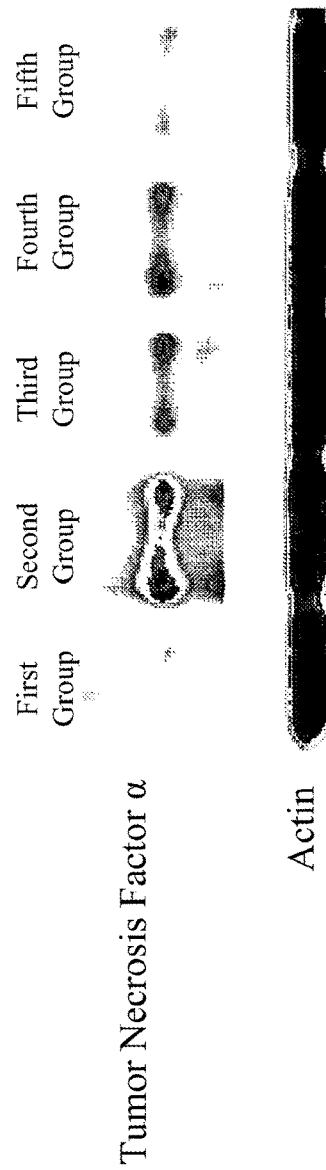
FIG. 25A shows the expression of tumor necrosis factor α in lung cells of rats in each group detected by western blotting.
Figure 25B:
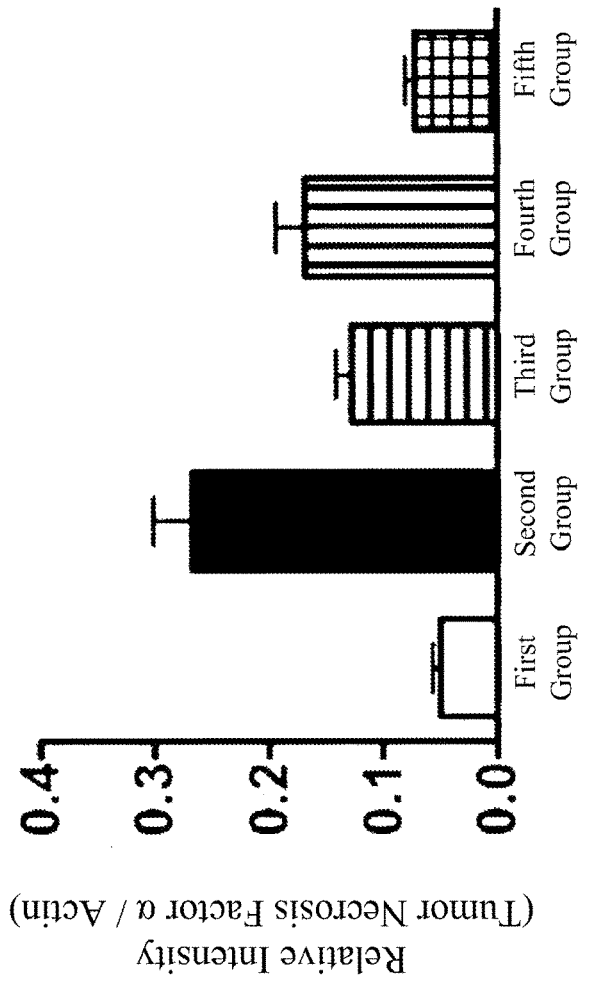
FIG. 25B shows the quantification results of the expression of tumor necrosis factor α of rats in each group in FIG. 25A.
Figure 26A:
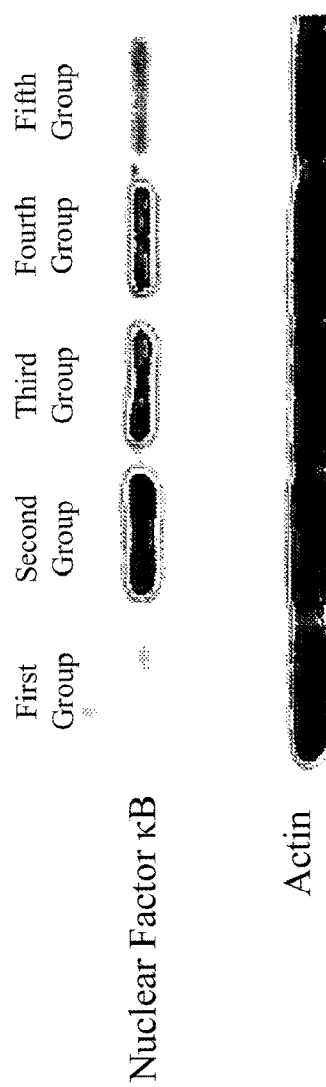
FIG. 26A shows the expression of nuclear factor κB in lung cells of rats in each group detected by western blotting.
Figure 26B:
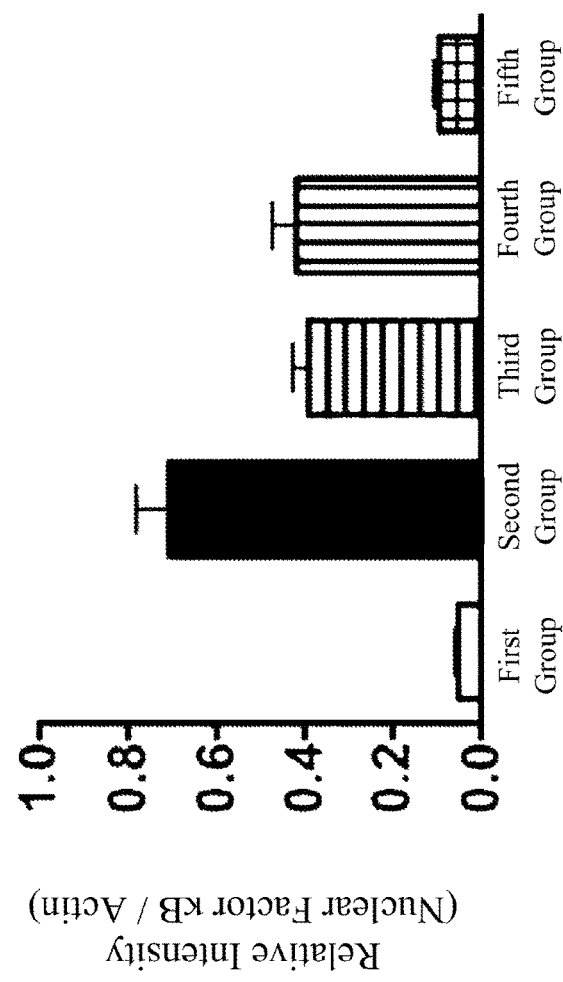
FIG. 26B shows the quantification results of the expression of nuclear factor κB of rats in each group in FIG. 26A.

As shown in FIG. 24 to FIG. 26, the expression levels of the inflammation indicator proteins: matrix metalloproteinase 9, nuclear factor κB, and tumor necrosis factor α were the lowest in the first group and the highest in the second group. The expression levels of the three inflammation indicator proteins of the fifth group were significantly lower than those of the second and fourth groups, and the expression levels of the three inflammation indicator proteins of the third group were significantly lower than those of the second and fourth groups.

Figure 27A:
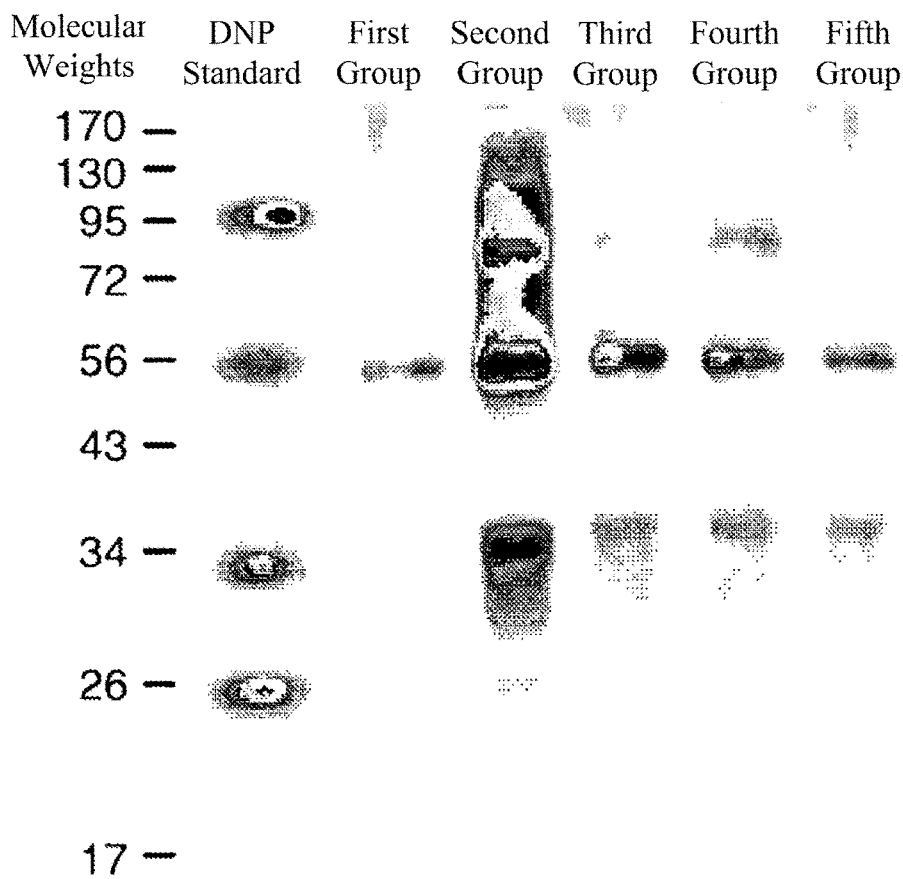
FIG. 27A shows the expression of oxidized proteins in lung cells of rats in each group.
Figure 27B:
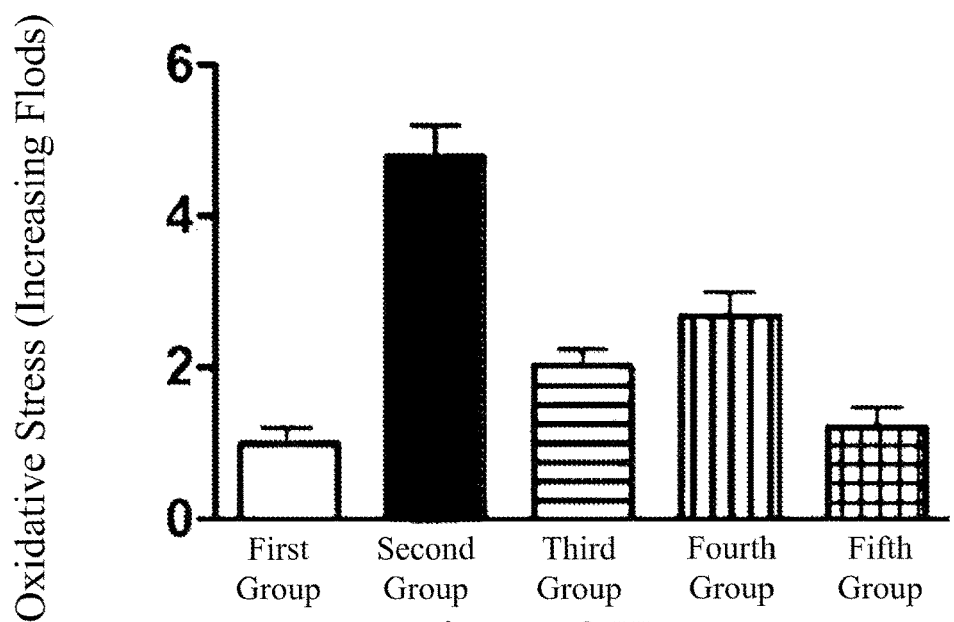
FIG. 27B shows the quantification results of the expression of oxidized proteins of rats in each group in FIG. 27A.

Please refer to FIG. 27, the oxidative stress of the second group was the highest among the five groups, the oxidative stress of the fifth group was significantly lower than that of the second to fourth groups, and the oxidative stress of the third group is significantly lower than that of the second and fourth groups.

Figure 28A:
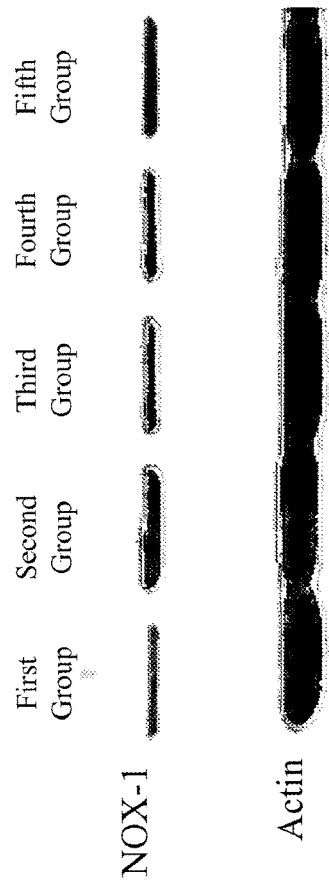
FIG. 28A shows the expression of NOX-1 in lung cells of rats in each group detected by western blotting.
Figure 28B:
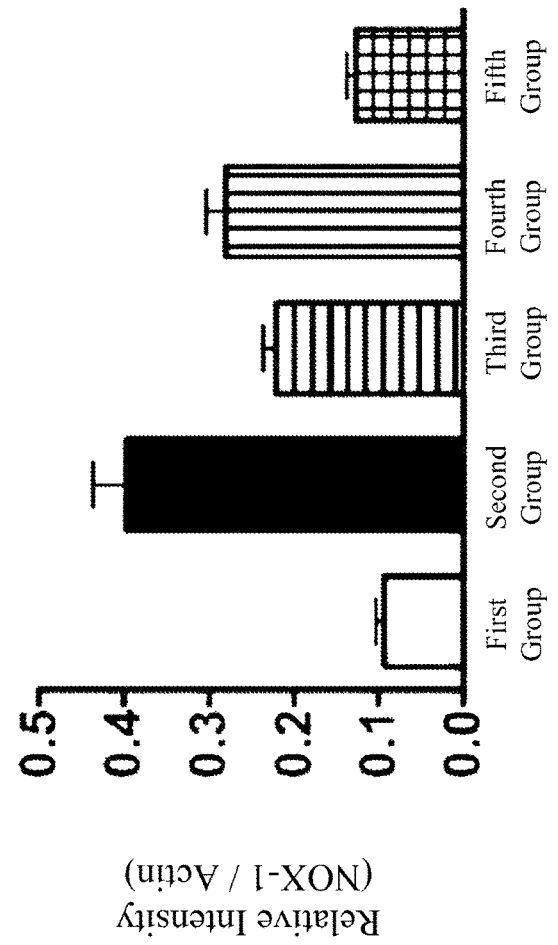
FIG. 28B shows the quantification results of the expression of NOX-1 of rats in each group in FIG. 28A.
Figure 29A:
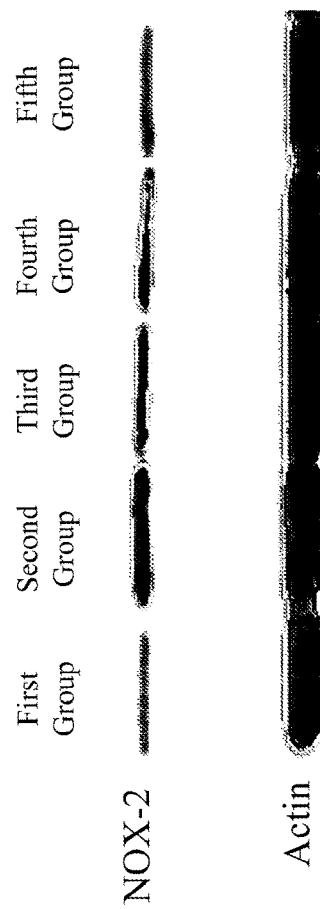
FIG. 29A shows the expression of NOX-2 in lung cells of rats in each group detected by western blotting.
Figure 29B:
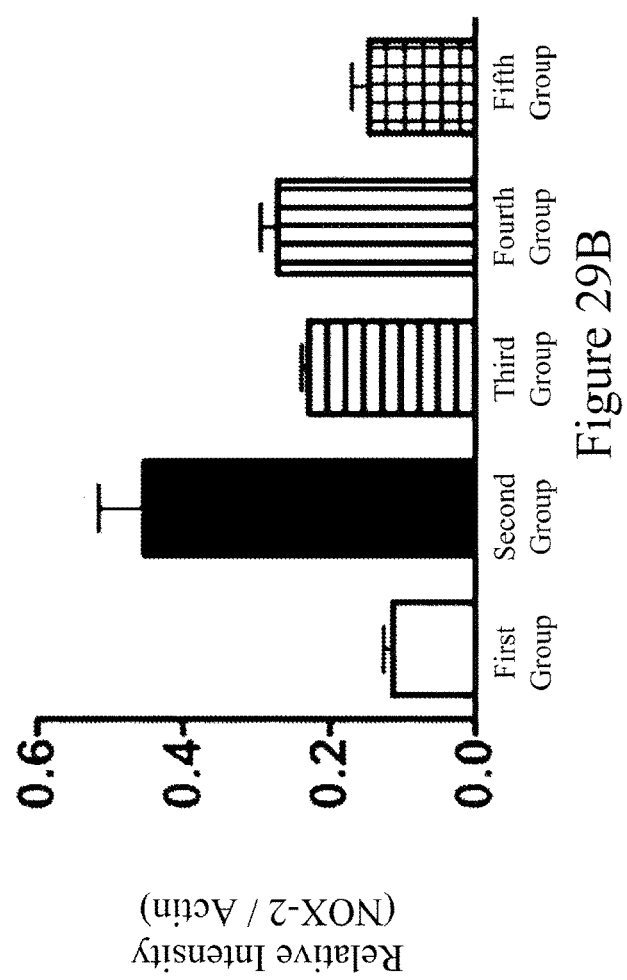
FIG. 29B shows the quantification results of the expression of NOX-2 of rats in each group in FIG. 29A.
Figure 30A:
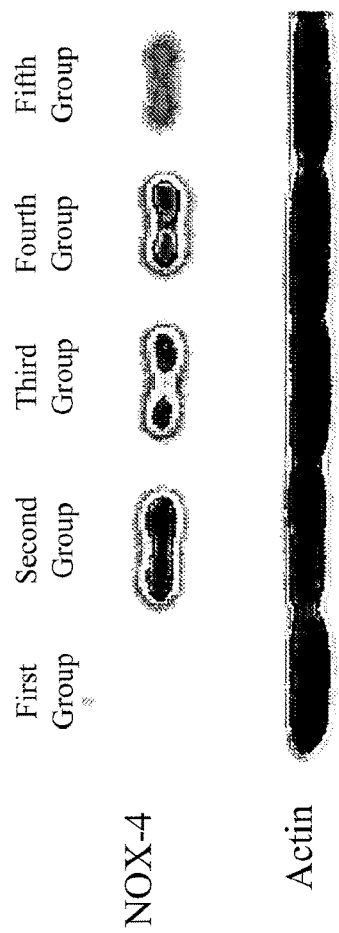
FIG. 30A shows the expression of NOX-4 in lung cells of rats in each group detected by western blotting.
Figure 30B:
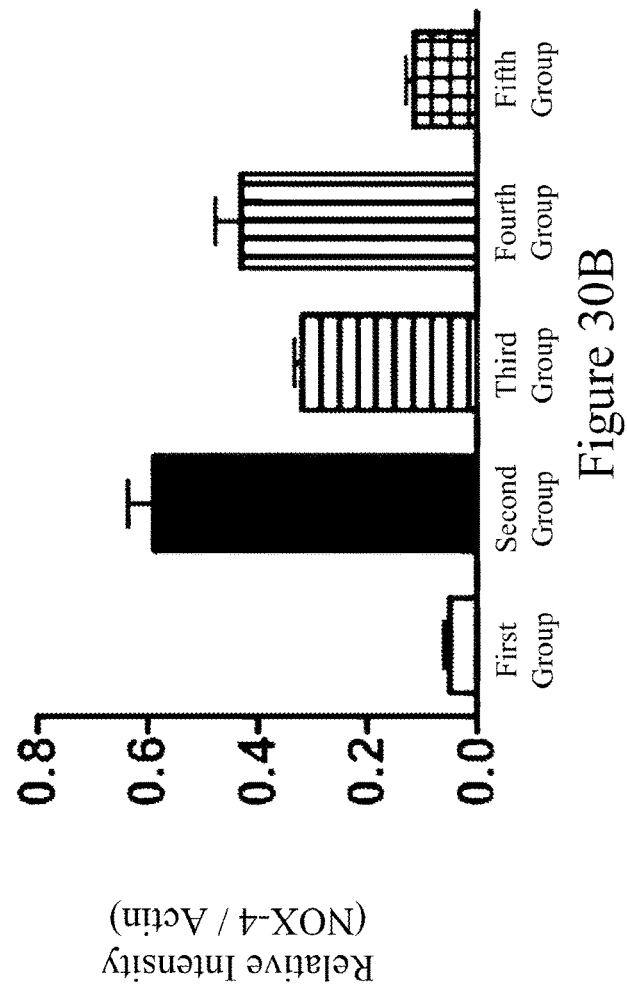
FIG. 30B shows the quantification results of the expression of NOX-4 of rats in each group in FIG. 30A.
Figure 31A:
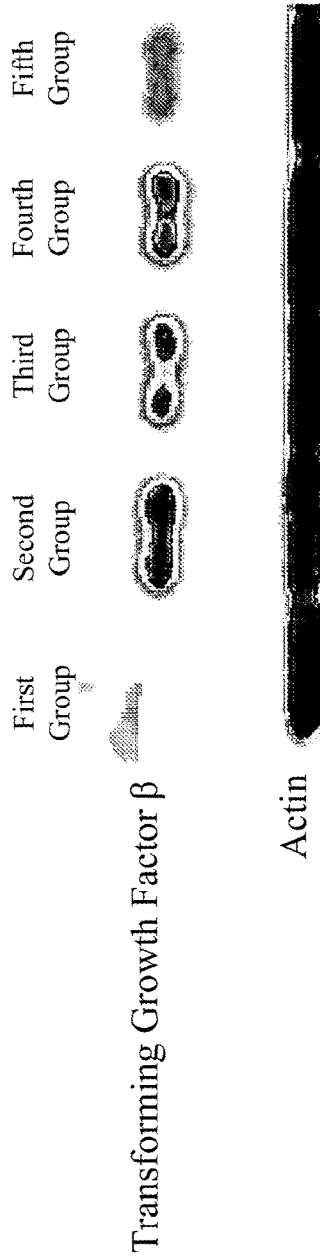
FIG. 31A shows the expression of transforming growth factor β in lung cells of rats in each group detected by western blotting.
Figure 31B:
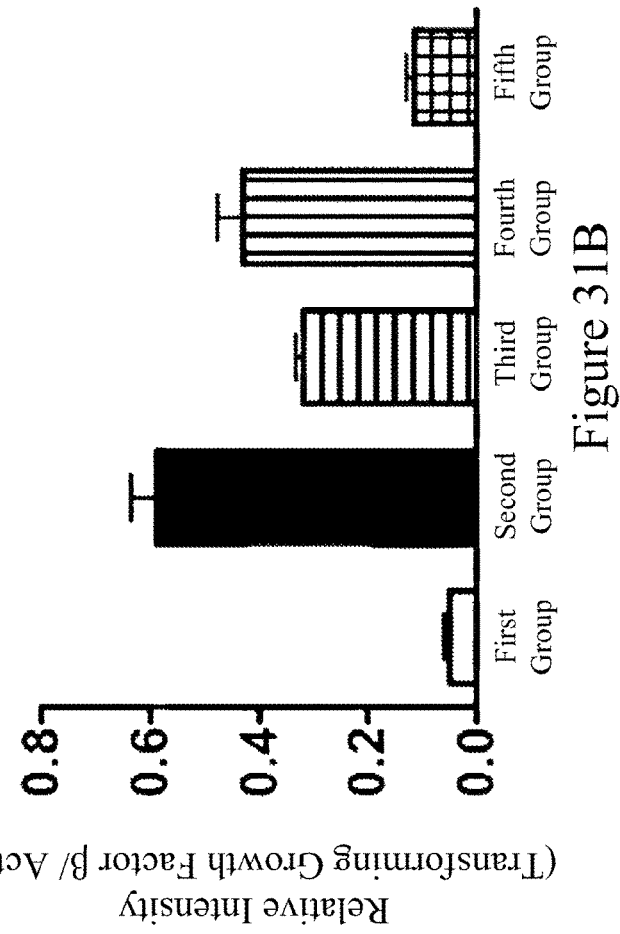
FIG. 31B shows the quantification results of the expression of transforming growth factor β of rats in each group in FIG. 31A.
Figure 32A:
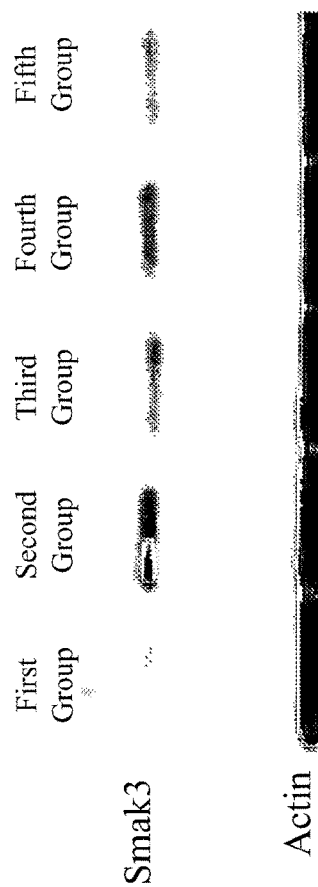
FIG. 32A shows the expression of Smad3 in lung cells of rats in each group detected by western blotting.
Figure 32B:
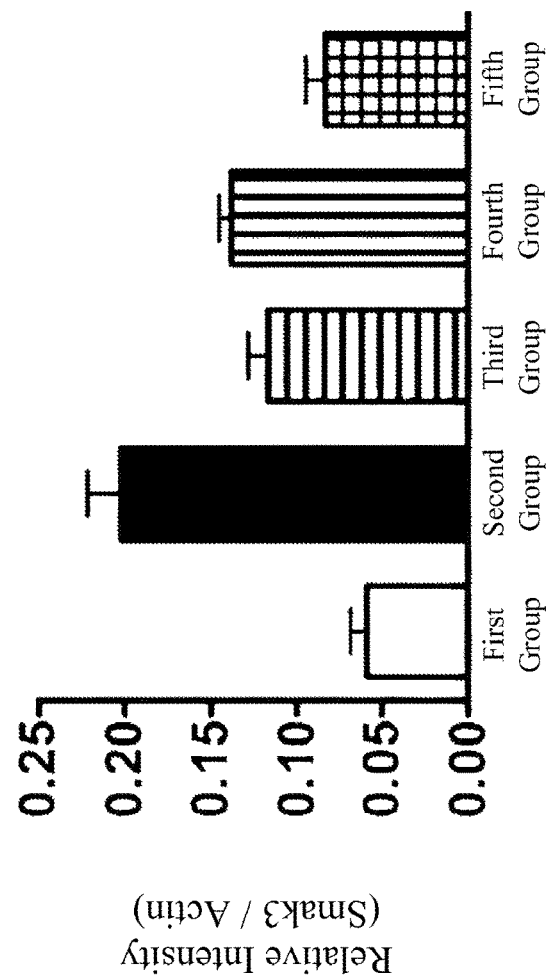
FIG. 32B shows the quantification results of the expression of Smad3 of rats in each group in FIG. 32A.
Figure 33A:
FIG. 33A shows the expression of bone morphogenetic protein-2 in lung cells of rats in each group detected by western blotting.
Figure 33B:
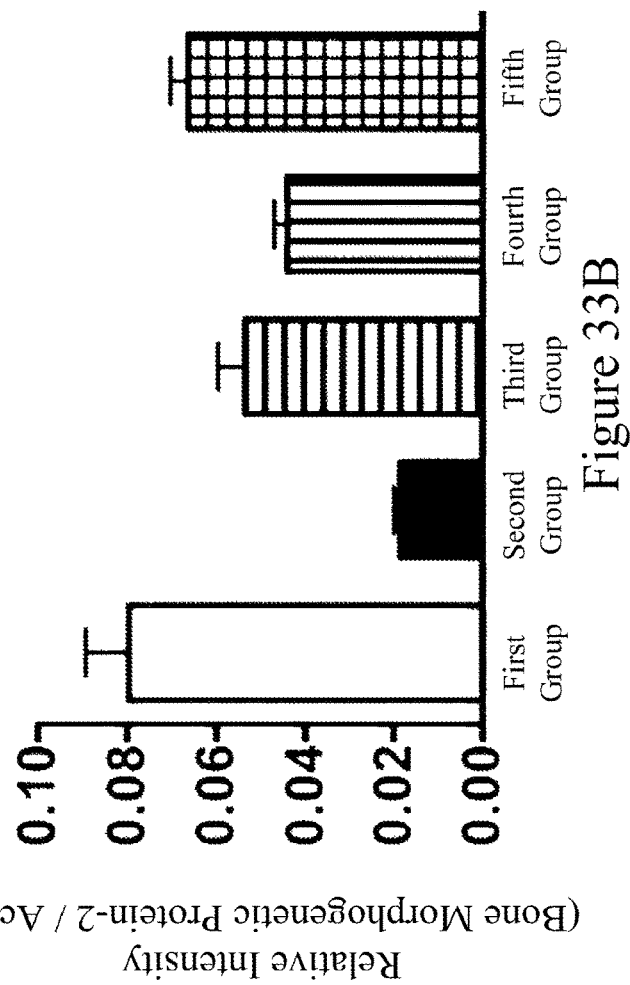
FIG. 33B shows the quantification results of the expression of bone morphogenetic protein-2 of rats in each group in FIG. 33A.
Figure 34A:
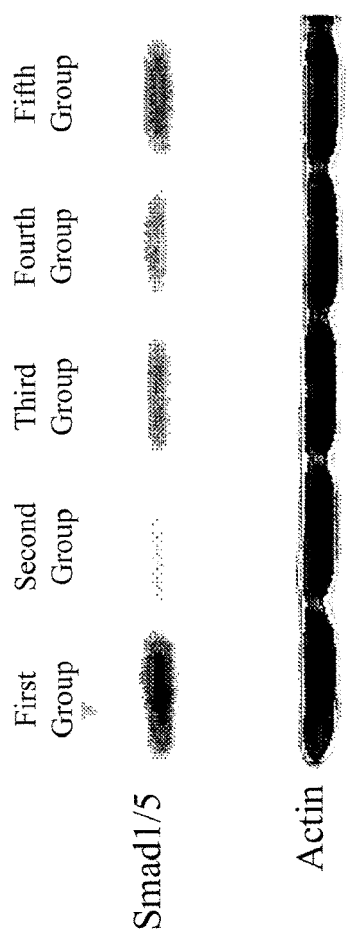
FIG. 34A shows the expression of Smad 1/5 in lung cells of rats in each group detected by western blotting.
Figure 34B:
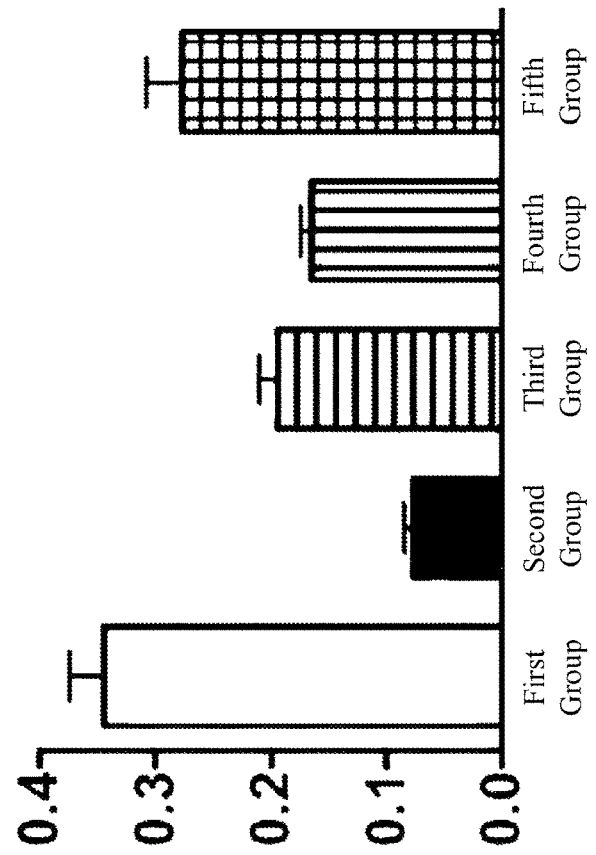
FIG. 34B shows the quantification results of the expression of Smad 1/5 of rats in each group in FIG. 34A.

As shown in FIG. 28 to FIG. 30, the expression levels of reactive oxygen species (ROS) indicator proteins: NOX-1, NOX-2, and NOX-4 were the lowest in the first group and the highest in the second group. The expression levels of the three ROS indicator proteins of the fifth group were significantly lower than those of the second to fourth groups, and the expression levels of the three ROS indicator proteins of the third group were significantly lower than those of the second and fourth groups.

Transforming growth factor β and Smad3 are fibrosis indicator proteins, whereas bone morphogenetic protein-2 and Smad 1/5 are anti-fibrosis indicator proteins. Please referring to FIG. 31 and FIG. 32, the expression levels of transforming growth factor β and Smad3 were the lowest in the first group and the highest in the second group; the expression levels of the fifth group were significantly lower than those of the second to fourth groups; the expression levels of the third group were significantly lower than those of the second and fourth groups. Comparing FIG. 33 and FIG. 34 with FIG. 31 and FIG. 32, the expression levels of bone morphogenetic protein-2 and Smad 1/5 in the lung parenchyma of the five groups were negatively correlated to the expression levels of transforming growth factor β and Smad3.

Figure 36A:
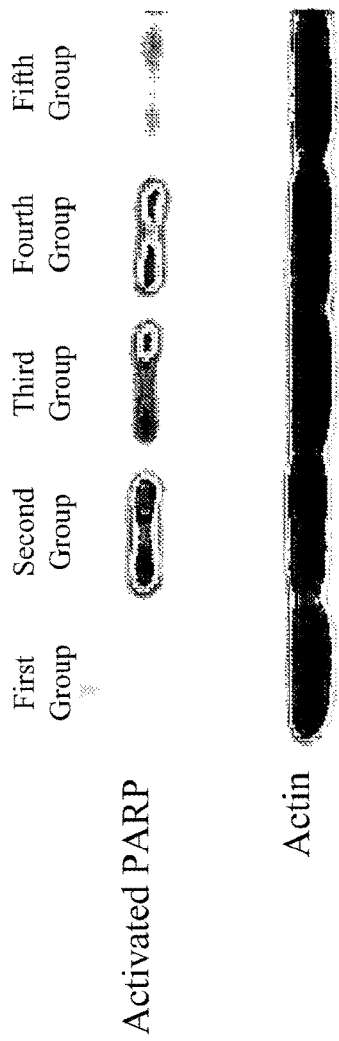
FIG. 36A shows the expression of activated PARP in lung cells of rats in each group detected by western blotting.
Figure 36B:
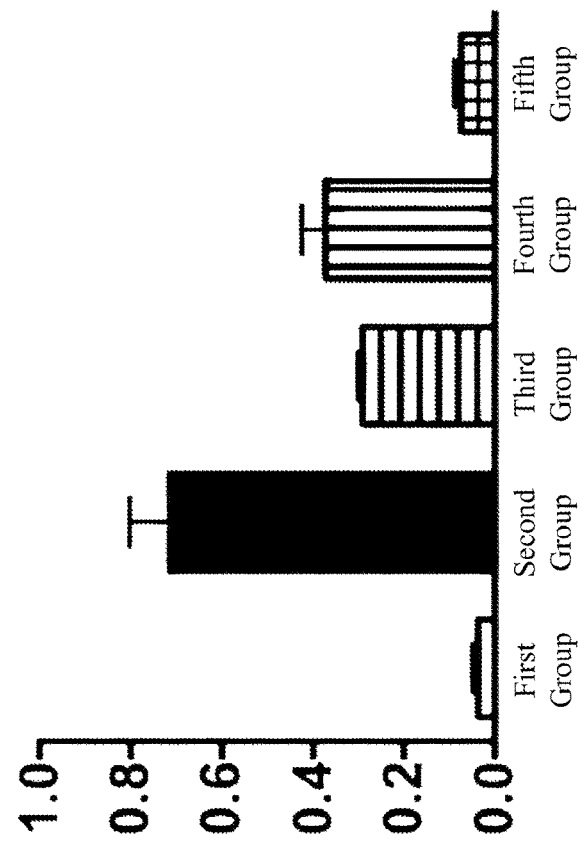
FIG. 36B shows the quantification results of the expression of activated PARP of rats in each group in FIG. 36A.
Figure 37A:
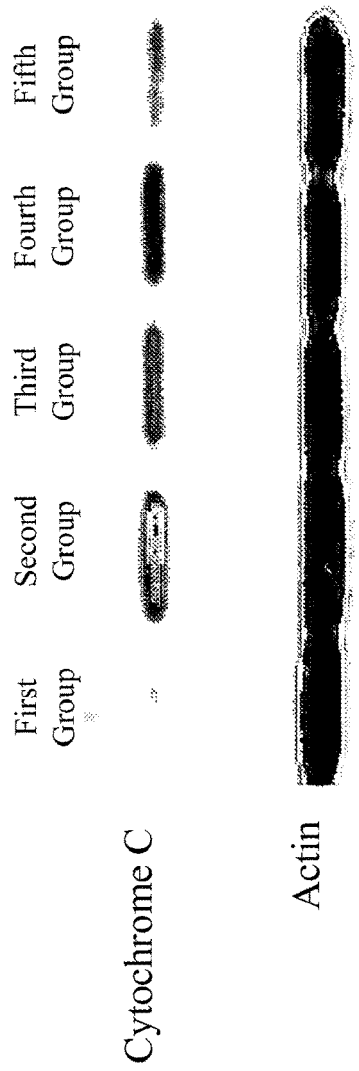
FIG. 37A shows the expression of cytochrome c in cytosol of lung cells of rats in each group detected by western blotting.
Figure 37B:
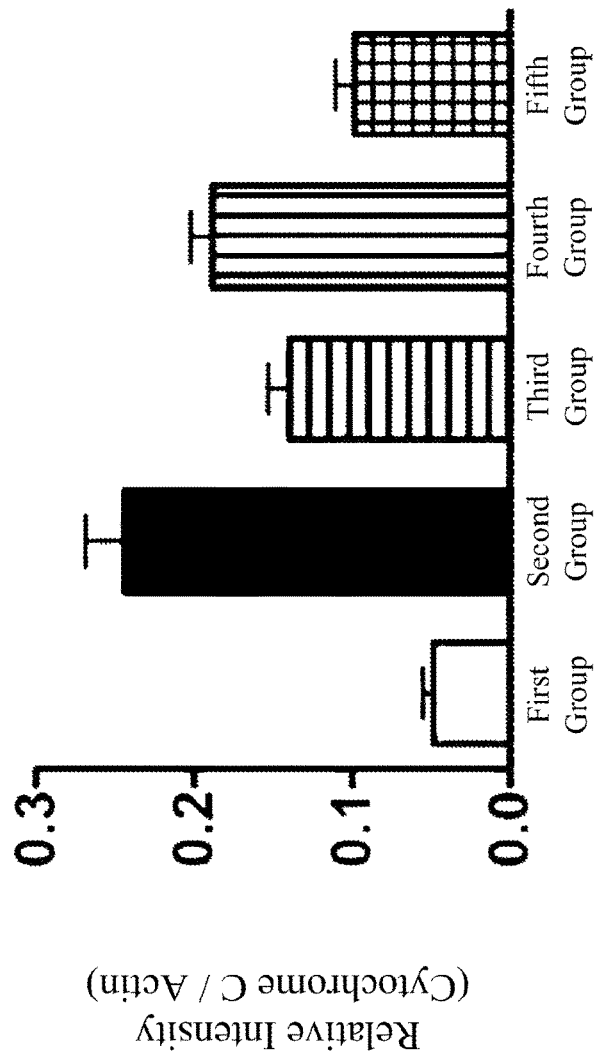
FIG. 37B shows the quantification results of the expression of cytochrome c in cytosol of lung cells of rats in each group in FIG. 37A.
Figure 38A:
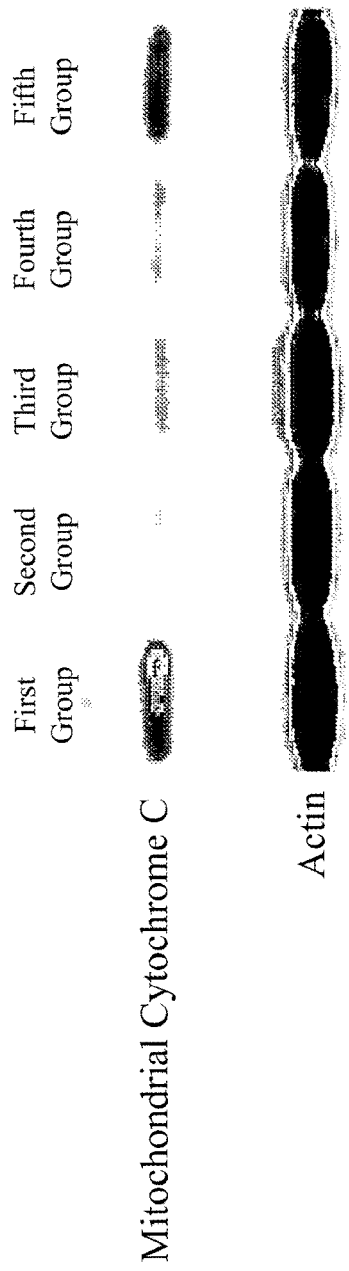
FIG. 38A shows the expression of cytochrome c in mitochondria in lung cells of rats in each group detected by western blotting.
Figure 38B:
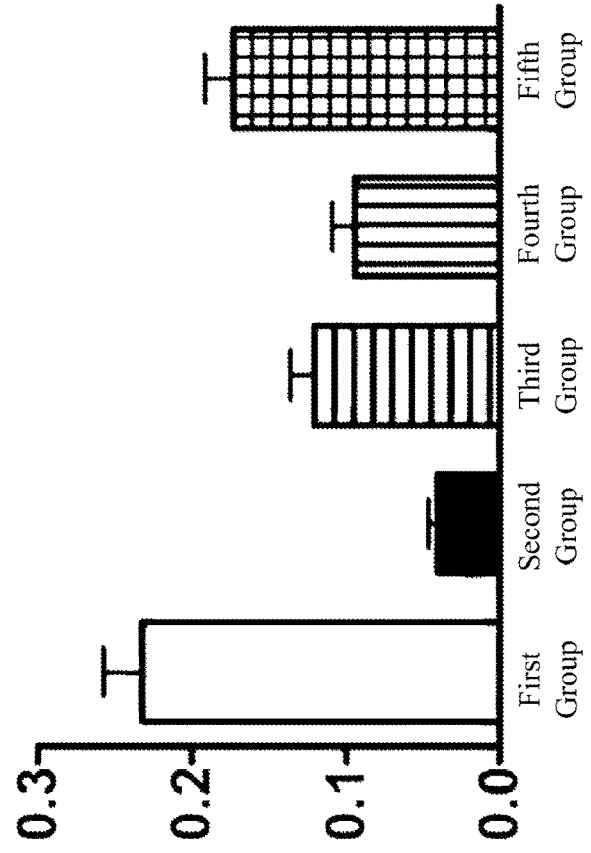
FIG. 38B shows the quantification results of the expression of cytochrome c in mitochondria in lung cells of rats in each group in FIG. 38A.
Figure 39A:
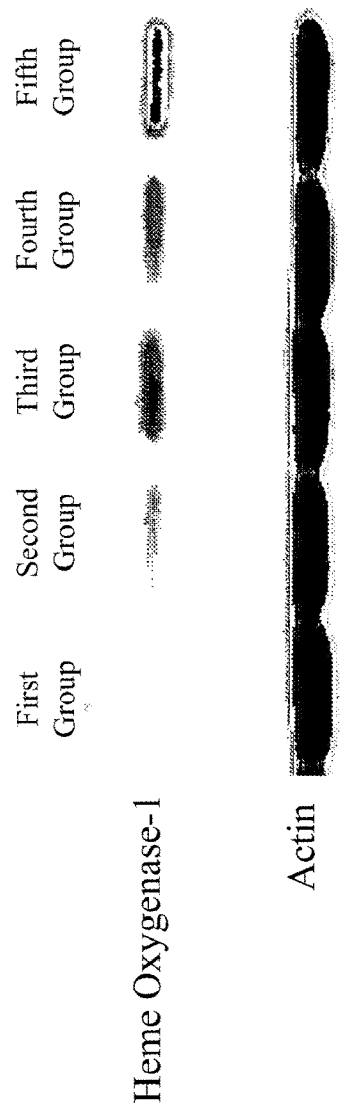
FIG. 39A shows the expression of heme oxygenase-1 (HO-1) in lung cells of rats in each group detected by western blotting.
Figure 39B:
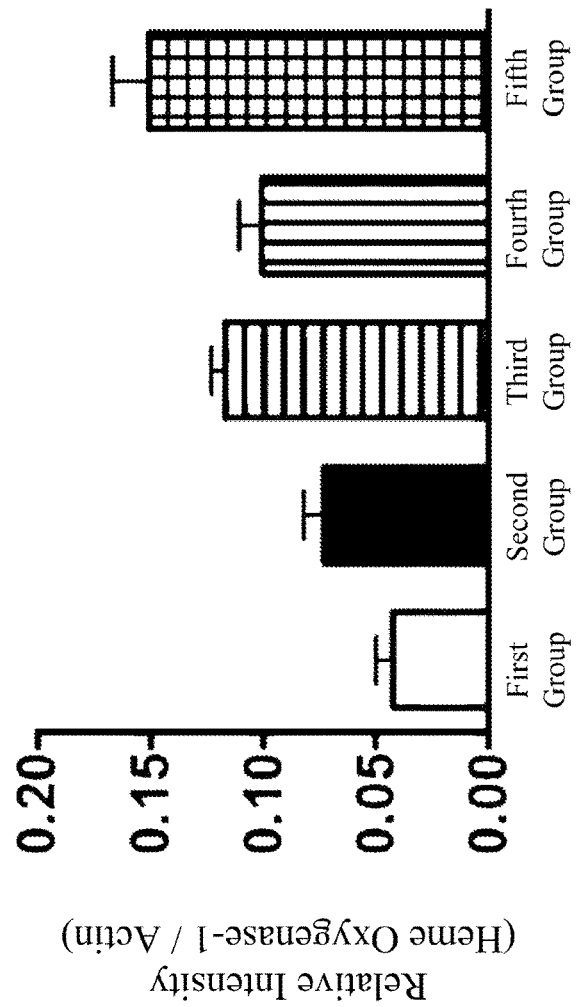
FIG. 39B shows the quantification results of the expression of heme oxygenase-1 (HO-1) of rats in each group in FIG. 39A.
Figure 40A:
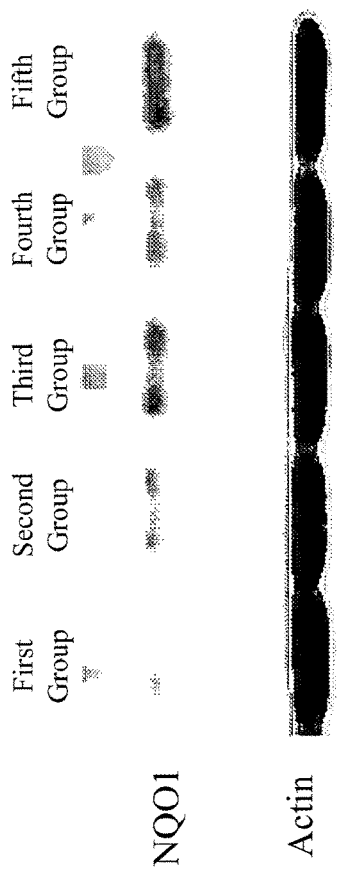
FIG. 40A shows the expression of NQO 1 in lung cells of rats in each group detected by western blotting.
Figure 40B:
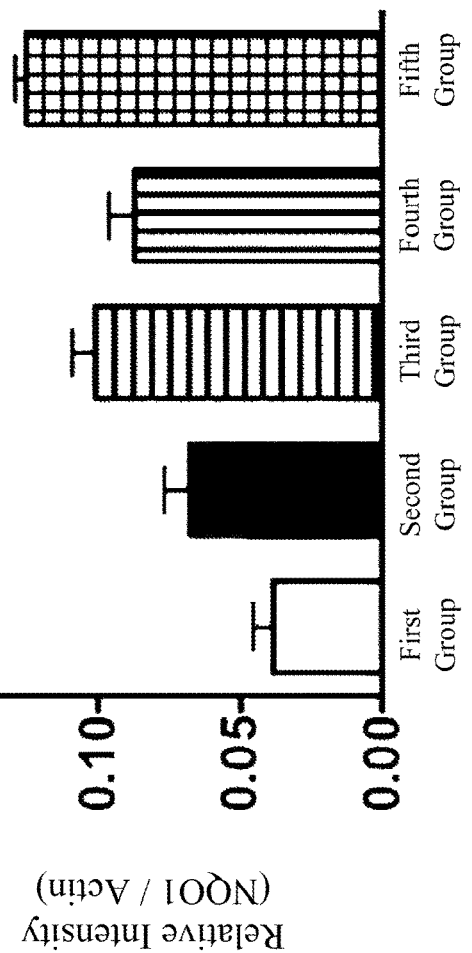
FIG. 40B shows the quantification results of the expression of NQO 1 of rats in each group in FIG. 40A.
Figure 41A:
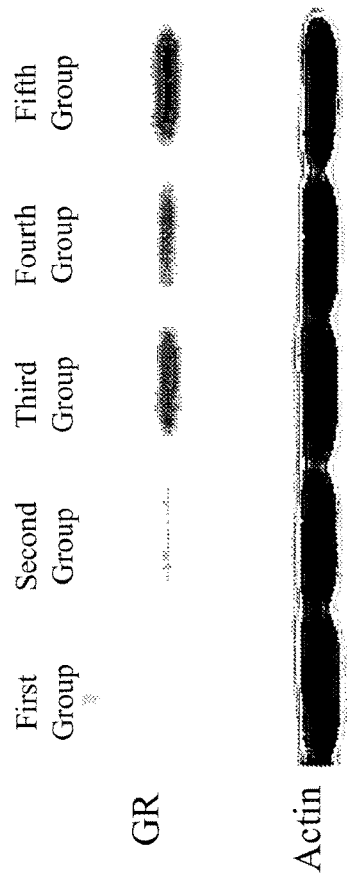
FIG. 41A shows the expression of GR in lung cells of rats in each group detected by western blotting.
Figure 41B:
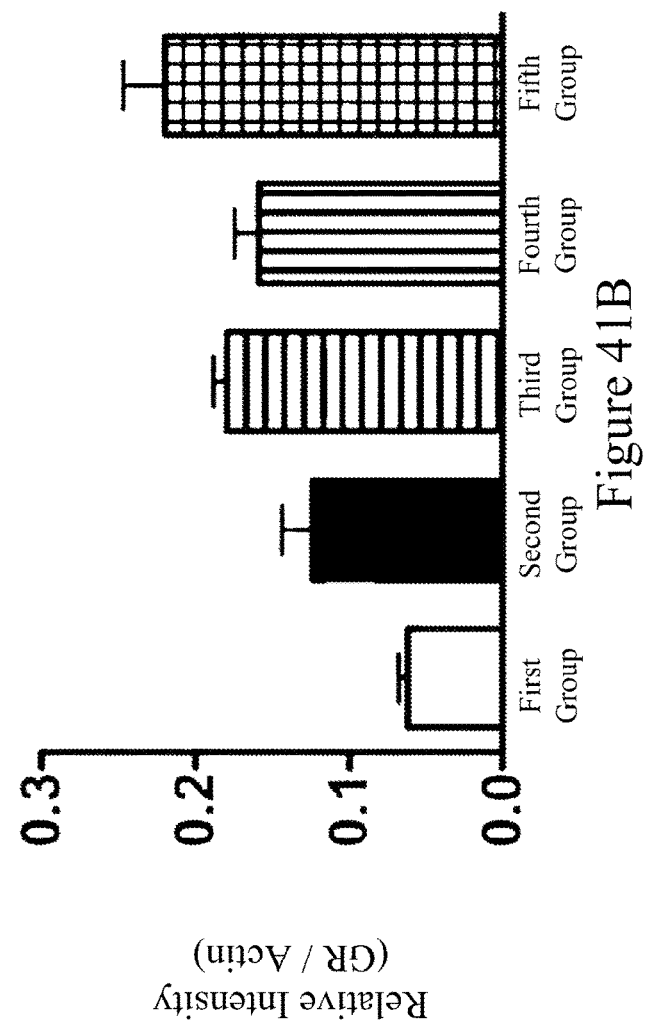
FIG. 41B shows the quantification results of the expression of GR of rats in each group in FIG. 41A.
Figure 42A:
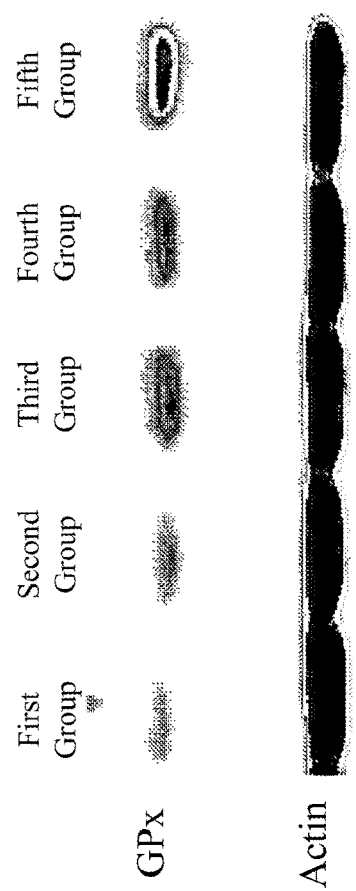
FIG. 42A shows the expression of GPx in lung cells of rats in each group detected by western blotting.
Figure 42B:
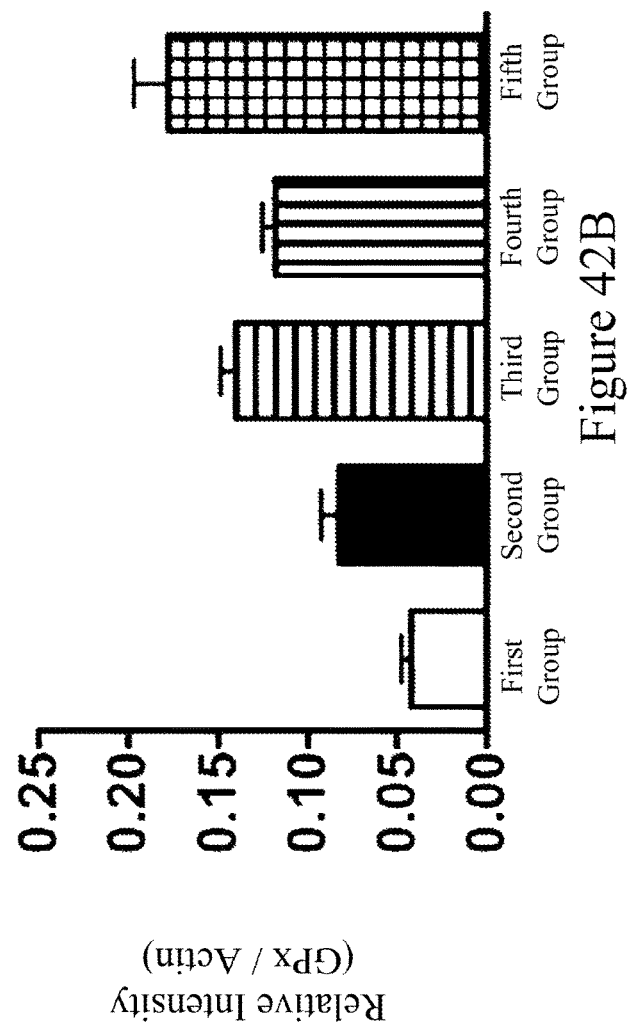
FIG. 42B shows the quantification results of the expression of GPx of rats in each group in FIG. 42A.

Please further refer to FIG. 35 to FIG. 37, the expression levels of the apoptosis indicator proteins: activated caspase-3, activated PARP, and cytochrome c were the lowest in the first group and the highest in the second group. The expression levels of the three apoptosis indicator proteins of the fifth group were significantly lower than those of the second and fourth groups, and the expression levels of the three apoptosis indicator proteins of the third group were significantly lower than those of the second and fourth groups. Since cytochrome c of mitochondria is an index of structural integrity of the mitochondria, as comparing FIG. 38 with FIG. 35 to FIG. 37, the expression levels of mitochondrial cytochrome c in the lung parenchyma of the five groups were negatively correlated to the expression levels of the three apoptosis indicator proteins.

Please refer to FIG. 39 to FIG. 42, the expression levels of the biomarkers of antioxidant, which are GR, GPx, NQO 1, and Heme oxygenase-1, were the lowest in the first group and the highest in the fifth group. The expression levels of the four biomarkers of antioxidant of the third group were significantly higher than those of the second and fourth groups.

From the above results, it was found that the expression levels of proteins related to apoptosis, fibrosis, and inflammation increased significantly in the lung parenchyma of rat model of acute respiratory distress syndrome, and the expression levels of ROS indicator proteins increased significantly as well, indicating that its lung cells are damaged or died, resulting in pulmonary dysfunction. By administering mitochondria or a composition containing mitochondria and melatonin, the introducing of mitochondria into damaged alveolar cells induced by pure oxygen can significantly reduce the expression levels of proteins related to apoptosis, fibrosis, and inflammation in the lung parenchyma, as well as reduce oxidative stress, damage in lung cells, or death. In addition, administration of a composition containing mitochondria and melatonin reached the best effects.

Accordingly, the pharmaceutical composition of the present invention is capable of reducing oxidative stress, suppressing inflammatory reaction, and reducing the death of lung epithelial cells, and therefore reaching the effect of treating severe lung injury and maintaining normal lung function.

Example 11: Dose Analysis

The rat model of acute respiratory distress syndrome was divided into two groups. One group was given 750 μg of mitochondria per rat, and the other group was given 1500 μg of mitochondria per rat. The two groups of rats were subjected to arterial blood gas test and hemodynamics test. The results are shown in Table 1 below.

TABLE 1

Test Results

| Dose of Mitochondria (μg/rat) | Oxygen Saturation (%) | Right ventricular systolic pressure (mmHg) |
| --- | --- | --- |
| 750 | 90 | 33 |
| 1500 | 93 | 36 |

As can be seen from the results in Table 1 above, the administration of high dose and low dose of mitochondria to the individual can achieve the desired effect of the present invention, in which a high dose can achieve a better effect.

From the above description, it is understood that, by delivering mitochondria into lung cells that are damaged or under oxidative stress, the pharmaceutical composition of the present invention can restore lung function, alleviate pulmonary parenchymal damage induced by acute respiratory distress syndrome, oxidative stress and apoptosis of alveolar epithelial cells, and reduce production of oxides, and thus improve or treat severe pulmonary parenchymal injury, such as increased lung crowded area, decreased number of alveolar sacs, and increased expression of Cx43 in alveolar epithelial cells. Furthermore, the previous study discloses that melatonin is an antioxidant, and it can be clearly understood from the results of the above examples that administration of the pharmaceutical composition of the present invention has a significantly improved effect compared to administration of melatonin only.

Accordingly, by administering an effective amount of the pharmaceutical composition of the present invention to an individual having a lung injury, it is possible to treat pulmonary parenchymal injury and restore the normal function of the lungs, and in which the administration of an effective amount of pharmaceutical compositions containing mitochondria and melatonin can achieve better efficacy.

The present invention has been illustrated in detail by way of example only. Many modifications or variations in the embodiments of the present invention made by those skilled in the art without departing from the spirit of the invention shall be covered within the scope of the appended claims.

REFERENCE

Brun-Buisson C, Minelli C, Bertolini G, Brazzi L, Pimentel J, Lewandowski K, Bion J, Romand J A, Villar J, Thorsteinsson A, et al: Epidemiology and outcome of acute-lung injury in European intensive care units. Results from the ALIVE study. *Intensive Care Med* 2004, 30:51-61.

Matthay M A, Zimmerman G A: Acute lung injury and the acute respiratory distress syndrome: four decades of inquiry into pathogenesis and rational management. *Am J Respir Cell Mol Biol* 2005, 33:319-327.

Rubenfeld G D, Caldwell E, Peabody E, Weaver J, Martin D P, Neff M, Stern E J, Hudson L D: Incidence and outcomes of acute lung injury. *N Engl J Med* 2005, 353: 1685-1693.

Phua J, Badia J R, Adhikari N K, Friedrich J O, Fowler R A, Singh J M, Scales D C, Stather D R, Li A, Jones A, et al: Has mortality from acute respiratory distress syndrome decreased over time?: A systematic review. *Am J Respir Crit Care Med* 2009, 179:220-227.

Ailawadi G, Lau C L, Smith P W, Swenson B R, Hennessy S A, Kuhn C J, Fedoruk L M, Kozower B D, Kron I L, Jones D R: Does reperfusion injury still cause significantmortality after lung transplantation? *J Thorac Cardiovasc Surg* 2009, 137:688-694.

Fiser S M, Tribble C G, Long S M, Kaza A K, Kern J A, Jones D R, Robbins M K, Kron I L: Ischemia-reperfusion injury after lung transplantation increases risk of late bronchiolitis obliterans syndrome. *Ann Thorac Surg* 2002, 73:1041-1047; discussion 1047-1048.

Ware L B, Matthay M A: The acute respiratory distress syndrome. *N Engl J Med* 2000, 342:1334-1349.

Ciesla D J, Moore E E, Johnson J L, Burch J M, Cothren C C, Sauaia A: The role of the lung in postinjury multiple organ failure. *Surgery* 2005, 138:749-757; discussion 757-748.

den Hengst W A, Gielis J F, Lin J Y, Van Schil P E, De Windt L J, Moens A L: Lung ischemia-reperfusion injury: a molecular and clinical view on a complex pathophysiological process. *Am J Physiol Heart Circ Physiol* 2010, 299:H1283-1299.

Choi W I, Shehu E, Lim S Y, Koh S O, Jeon K, Na S, Lim C M, Lee Y J, Kim S C, Kim I H, et al: Markers of poor outcome in patients with acute hypoxemic respiratory failure. *J Crit Care* 2014.

Dolinay T, Kim Y S, Howrylak J, Hunninghake G M, An C H, Fredenburgh L, Massaro A F, Rogers A, Gazourian L, Nakahira K, et al: Inflammasome-regulated cytokines are critical mediators of acute lung injury. *Am J Respir Crit Care Med* 2012, 185:1225-1234.

Bhargava M, Wendt C H: Biomarkers in acute lung injury. *Transl Res* 2012, 159:205-217.

Sun C K, Yen C H, Lin Y C, Tsai T H, Chang L T, Kao Y H, Chua S, Fu M, Ko S F, Leu S, Yip H K: Autologous transplantation of adipose-derived mesenchymal stem cells markedly reduced acute ischemia-reperfusion lung injury in a rodent model. *J Transl Med* 2011, 9:118.

Budinger G R, Mutlu G M, Urich D, Soberanes S, Buccellato L J, Hawkins K, Chiarella S E, Radigan K A, Eisenbart J, Agrawal H, et al: Epithelial cell death is an important contributor to oxidant-mediated acute lung injury. *Am J Respir Crit Care Med* 2011, 183:1043-1054.

Yip H K, Chang Y C, Wallace C G, Chang L T, Tsai T H, Chen Y L, Chang H W, Leu S, Zhen Y Y, Tsai C Y, et al: Melatonin treatment improves adipose-derived mesenchymal stem cell therapy for acute lung ischemia-reperfusion injury. *J Pineal Res* 2013, 54:207-221.

What is claimed is:

1. A method for treating lung injury and/or diseases related to lung injury in a subject in need thereof, comprising:
    administering a pharmaceutical composition to the subject in need thereof, wherein the pharmaceutical composition comprises an effective amount of mitochondria, an effective amount of melatonin, and at least one pharmaceutically acceptable carrier.

2. The method of claim 1, wherein the diseases related to lung injury are selected from the group consisting of pneumonia, atelectasis, dyspnea, pulmonary fibrosis, and pulmonary edema.

3. The method of claim 1, wherein lung injury is acute respiratory distress syndrome.

* * * * *